United States Patent [19]

Häbich et al.

[11] Patent Number: 5,646,121

[45] Date of Patent: Jul. 8, 1997

[54] PSEUDOPEPTIDES WITH ANTIVIRAL ACTIVITY

[75] Inventors: Dieter Häbich, Wuppertal; Thomas-J. Schulze, Köln; Jürgen Reefschläger; Jutta Hansen, both of Wuppertal; Rainer Neumann, Köln; Gert Streissle, Wuppertal; Arnold Paessens, Haan, all of Germany

[73] Assignee: Bayer Aktiengesellschaft, Leverkusen, Germany

[21] Appl. No.: 302,064

[22] Filed: Sep. 7, 1994

[30] Foreign Application Priority Data

Sep. 14, 1993 [DE] Germany .................. 43 31 134.2

[51] Int. Cl.$^6$ .................. C07D 241/04; C07D 211/06; A61K 31/16; A61K 31/165
[52] U.S. Cl. .................. 514/18; 514/19; 544/353; 544/224; 544/335; 530/331; 546/335; 546/336; 546/175; 546/146; 546/147; 548/568; 548/324.1; 548/255; 549/53; 549/407
[58] Field of Search .................. 514/18, 19; 544/353, 544/224, 335; 530/331; 546/335, 336, 175, 146, 147; 548/568, 324.1, 255; 549/53, 407

[56] References Cited

U.S. PATENT DOCUMENTS

| | | | |
|---|---|---|---|
| 4,107,158 | 8/1978 | Lefrancier | 260/112.5 |
| 4,119,493 | 10/1978 | Isowa et al. | 195/29 |
| 4,125,606 | 11/1978 | Bornstein | 424/178 |
| 4,929,736 | 5/1990 | Groutas | 548/341 |
| 5,086,069 | 2/1992 | Klein et al. | 514/399 |
| 5,153,176 | 10/1992 | Abe et al. | 514/18 |
| 5,380,713 | 1/1995 | Balasubramanian et al. | 514/18 |
| 5,492,896 | 2/1996 | Häbich et al. | 514/18 |

FOREIGN PATENT DOCUMENTS

| | | |
|---|---|---|
| 488041 | 11/1991 | European Pat. Off. |
| 611776 | 2/1994 | European Pat. Off. |
| 217103 | 8/1986 | United Kingdom. |
| 9222570 | 6/1992 | WIPO. |

OTHER PUBLICATIONS

The Journal of Antibiotics vol. XLI No. 8, pp. 1019–1028, (Aug. 1988) Gomi et al.

J.C.S. Chem. Comm, 1976, pp. 451–452. Matsuura et al.

J. Org. Chem. 1985, 50, 2198–2200, Robert E. Ireland and Daniel W. Norbeck.

J. Chem. Research (S), 1988, Choji Kashima, et al.

The EMBO Journal, vol. 7, No. 6, pp. 1785–1791, 1988, Jutta Hansen, et al.

J. Org. Chem., vol. 42, No. 20, 1977, Daniel F. Veber, et al.

Chemical Abstracts, vol. 115, Sep. 2, 1991, No. 9, 115:92899u Raju Mohan et al.

Munekata et al., Bulletin of the Chemical Society of Japan, 46(10), 1973, 3187–3193.

Place, Biochimica Biophysica ACTA, 925(2), 1987, 185–193.

Nishino et al., Journal of Biochemistry (Tokyo), 75(5), 1974, 979–985.

*Primary Examiner*—Matthew V. Grumbling
*Attorney, Agent, or Firm*—Sprung Horn Kramer & Woods

[57] ABSTRACT

The present invention relates to novel pseudopeptides with antiviral activity of the general formula (I)

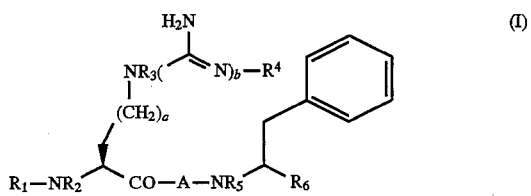

in which the substituents have the meaning given in the description, to a process for their preparation, and to their use as antiviral agents, especially against cytomegaloviruses.

9 Claims, No Drawings

PSEUDOPEPTIDES WITH ANTIVIRAL ACTIVITY

The present invention relates to novel pseudopeptides with antiviral activity, to processes for their preparation and to their use as antiviral agents, in particular against cytomegaloviruses.

Peptide aldehydes which are inhibitors of the HIV protease and of picornavirus proteases are described in the publications J. Antibiot. 44, 1019 (1991), FEBS Letters 3, 253 (1993), as well as in patent application WO 92/22570. Furthermore, peptide aldehydes have been described which are inhibitors of serine proteases [U.S. Pat. No. 5,153,176; EP 526,877].

Various nucleoside and nucleotide analogs, anthraquinone derivatives, cobalt complexes, macrolides and acyl peptides [EP 488,041] represent classes of compounds which are known to possess anti-cytomegalovirus activity.

The present invention now relates to novel pseudopeptides which possess antiviral activity and are of general formula (I)

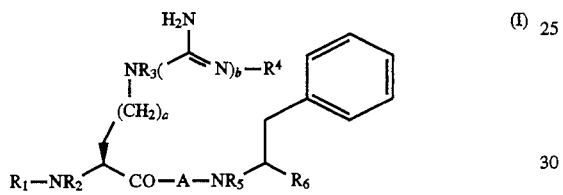

in which a represents a number 1, 2 or 3, b represents a number 0 or 1, $R^1$ represents hydrogen, or represents an amino protective group, or represents a radical of the formula $R^7-NR^8-CO-$, $R^9-(CH_2)_c-CO-$, $R^{10}-(CH_2)_d-O-CO-$, or represents a radical of the formula $-SO_2-R^{11}$, in which $R^7$ denotes cycloalkyl having 3 to 6 carbon atoms, or denotes straight-chain or branched alkyl having up to 18 carbon atoms which is optionally substituted by hydroxyl, straight-chain or branched alkoxy having up to 4 carbon atoms, halogen, trifluoromethyl, trifluoromethoxy or cycloalkyl having 3 to 6 carbon atoms, or by aryl having 6 to 10 carbon atoms which, for its part, can be substituted identically or differently up to 2 times by carboxyl, cyano, hydroxyl, halogen, perhalogenoalkyl having up to 5 carbon atoms, or by straight-chain or branched acyl, alkoxy or alkoxy carbonyl having in each case up to 6 carbon atoms, or alkyl is optionally substituted by a group of the formula $-CO_2R^{12}$, in which denotes hydrogen, or straight-chain or branched alkyl or alkenyl having in each case up to 8 carbon atoms which are optinally substituted by phenyl, or $R^7$ denotes aryl having 6 to 10 carbon atoms which is optionally substituted identically or differently up to 3 times by carboxyl, amino, halogen, hydroxyl, cyano, perhalogenoalkyl having up to 5 carbon atoms, or by straight-chain or branched acyl, alkoxy, vinyl alkoxy carbonyl, alkoxycarbonyl or having in each case up to 6 carbon atoms, which, for its part, is substituted by straight-chain or branched alkoxy having up to 6 carbon atoms, or denotes an amino acid radical of the formula

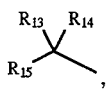

in which $R^{13}$ and $R^{14}$ are identical or different and denote hydrogen or methyl, or $R^{13}$ and $R^{14}$ together form a 5- or 6-membered saturated carbocyclic ring, or $R^{13}$ denotes hydrogen or methyl, and $R^{14}$ denotes cycloalkyl having 3 to 8 carbon atoms or aryl having 6 to 10 carbon atoms, or hydrogen, or straight-chain or branched alkyl having up to 8 carbon atoms where the alkyl is optionally substituted by methylthio, hydroxyl, mercapto or guanidyl, or by a group of the formula $-NR^{16}R^{17}$ or $R^{18}-OC-$, in which $R^{16}$ and $R^{17}$, independently of each other, denote hydrogen, straight-chain or branched alkyl having up to 8 carbon atoms, or phenyl, and denotes hydroxyl, benzyloxy, alkoxy having up to 6 carbon atoms, or the above listed group $-NR^{16}R^{17}$, $R^{15}$ denotes straight-chain or branched alkyl having up to 8 carbon atoms which is optionally substituted by hydroxyl or straight-chain or branched alkoxy having up to 6 carbon atoms, or denotes carboxyl, allyloxycarbonyl, straight-chain or branched alkoxycarbonyl having up to 8 carbon atoms, or benzyloxycarbonyl, or the alkyl is optionally substituted by cycloalkyl having 3 to 8 carbon atoms, or by aryl having 6 to 10 carbon atoms which, for its part, is optionally substituted by hydroxyl, halogen, nitro, alkoxy having up to 8 carbon atoms, or by the group $-NR^{16}R^{17}$, in which $R^{16}$ and $R^{17}$ have the abovementioned meaning, or the alkyl is optionally substituted by a 5- to 6-membered nitrogen-containing heterocycle or indolyl, in which the corresponding $-NH-$ functions are optionally protected by alkyl having up to 6 carbon atoms or by an amino protective group, or $R^7$ denotes a radical of the formula

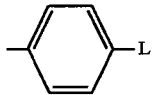

in which

L denotes phenyl or pyridyl, $R^8$ denotes hydrogen, straight-chain or branched alkyl having up to 6 carbon atoms, or an aminoprotective group, $R^9$ denotes straight-chain or branched alkyl having up to 8 carbon atoms, which is optionally substituted by pyridyl, or aryloxy or aryl having in each case 6 to 10 carbon atoms, indolyl, quinolyl, quinoxalinyl, isoquinolyl, or a 5- to 7-membered, saturated or unsaturated, heterocycle having up to 3 heteroatoms selected from the group comprising S, N or O, where the cycles can be substituted identically or differently up to 3 times by carboxyl, cyano, hydroxyl, halogen, amino, nitro, methylamino, or perhalogenoalkyl having up to 5 carbon atoms, or by straight-chain or branched alkyl, acyl, alkoxy or alkoxycarbonyl having in each case up to 6 carbon atoms, or aryl is also optionally substituted by a 5- to 7-membered, saturated or unsaturated, heterocycle having up to 3 heteroatoms selected from the group comprising S, N or O, which, for its part, can be substituted by phenyl, or $R^9$ denotes a radical of the formula

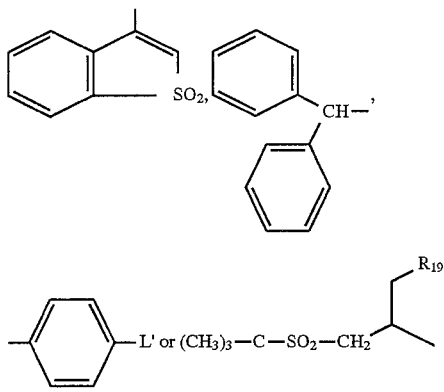

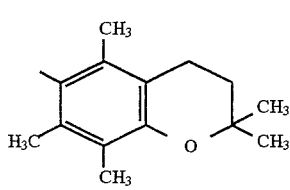

in which

L' has the abovementioned meaning of L and is identical to or different from the latter, $R^{19}$ denotes phenyl or naphthyl, c denotes a number 0, 1, 2 or 3, d denotes a number 0, 1, 2 or 3, $R^{10}$ has the abovementioned meaning of $R^9$ and is identical to or different from the latter, $R^{11}$ denotes methyl, phenyl or naphthyl which is optionally substituted identically or differently up to 4 times by methyl or methoxy, or denotes a radical of the formula

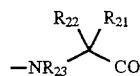

$R^2$, $R^3$ and $R^5$ are identical or different and represent hydrogen or straight-chain or branched alkyl having up to 4 carbon atoms, or represent an aminoprotective group, $R^4$ represents hydrogen, nitro, or an aminoprotective group, or a radical of the formula —$SO_2$—$R^{20}$, in which $R^{20}$ has the abovementioned meaning of $R^{11}$ and is identical to or different from the latter, A represents a bond or a radical of the formula $$-NR_{23}\overset{R_{22}\ \ R_{21}}{\diagup\!\!\!\diagdown}CO$$

in which $R^{21}$ and $R^{22}$ are identical or different and have the abovementioned meaning of $R^{13}$ and $R^{14}$ and are identical to or different from the latter, $R^{23}$ has the abovementioned meaning of $R^2$, $R^3$ or $R^5$, and is identical to or different from the latter, $R^6$ represents formyl or carboxyl, or represents straight-chain or branched alkoxycarbonyl having up to 8 carbon atoms, or represents a radical of the formula —$CH_2$—$OR^{24}$ or —$CH(OR^{25})_2$, in which $R^{24}$ and $R^{25}$ are identical or different and denote hydrogen, straight-chain or branched alkyl having up to 6 carbon atoms, or a hydroxyl protective group, and salts thereof, with the proviso that A must not represent valine.

The compounds of the general formula (I) according to the invention may also be present in the form of their salts. In general, salts with organic and inorganic bases or acids may be mentioned here.

The acids which can be added on preferably include hydrohalic acids, such as, for example, hydrofluoric acid, hydrochloric acid and hydrobromic acid, in particular hydrofluoric and hydrochloric acids, and, additionally, phosphoric acid, nitric acid and sulphuric acid, and monofunctional and bifunctional carboxylic acids and hydroxycarboxylic acids, such as, for example, acetic acid, maleic acid, malonic acid, oxalic acid, gluconic acid, succinic acid, fumaric acid, tartaric acid, citric acid, salicylic acid, sorbic acid and lactic acid, as well as sulphonic acids, such as, for example, p-toluenesulphonic acid, 1,5-naphthalenedisulphonic acid or camphorsulphonic acid.

Physiologically harmless salts can also be metal or ammonium salts of the compounds according to the invention which possess a free carboxyl group. Those which are particularly preferred are, for example, sodium, potassium, magnesium or calcium salts, as well as ammonium salts which are derived from ammonia or organic amines, such as, for example, ethylamine, diethylamine, triethylamine, diethanolamine, triethanolamine, dicyclohexylamine, dimethylaminoethanol, arginine, lysine or ethylenediamine.

Within the scope of the abovementioned definition, hydroxyl protective group generally represents a protective group from the series: tert-butoxydiphenylsilyl, trimethylsilyl, triethylsilyl, triisopropylsilyl, tertbutyldimethylsilyl, tert-butyldiphenylsilyl, triphenylsilyl, trimethylsilylethoxycarbonyl, benzyl, benzyloxycarbonyl, 2-nitrobenzyl, 4-nitrobenzyl, 2-nitrobenzyloxycarbonyl, 4-nitrobenzyloxycarbonyl, tert-butyloxycarbonyl, allyloxycarbonyl, 4-methoxybenzyl, 4-methoxybenzyloxycarbonyl, formyl, acetyl, trichloroacetyl, 2,2,2-trichloroethoxycarbonyl, 2,4-dimethoxybenzyl, 2,4-dimethoxybenzyloxycarbonyl, methylthiomethyl, methoxyethoxymethyl, [2-(trimethylsilyl)ethoxy]methyl, 2-(methylthiomethoxy) ethoxycarbonyl, benzoyl, 4-methylbenzoyl, 4-nitrobenzoyl, 4-fluorobenzoyl, 4-chlorobenzoyl or 4-methoxybenzoyl. Acetyl, benzoyl, benzyl or methylbenzyl are preferred.

Within the scope of the invention, amino protective groups are the aminoprotective groups which are customarily used in peptide chemistry.

These preferably include: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, allyloxycarbonyl, vinyloxycarbonyl, 2-nitrobenzyloxycarbonyl, 3,4,5-trimethoxybenzyloxycarbonyl, cyclohexyloxycarbonyl, 1,1-dimethyloxycarbonyl, adamantylcarbonyl, phthaloyl, 2,2,2- trichloroethoxycarbonyl, 2,2,2-trichloro-tert-butoxycarbonyl, menthyloxycarbonyl, phenoxycarbonyl, 4-nitrophenoxycarbonyl, fluoroenyl-9-methoxycarbonyl, formyl, acetyl, propionyl, pivaloyl, 2-chloroacetyl, 2-bromoacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl or 4-nitrophenyl.

Heterocycle generally represents a 5- to 7-membered, preferably 5- to 6-membered, saturated or unsaturated, ring, which, as hetero atoms, can contain up to 3 oxygen, sulphur and/or nitrogen atoms. 5- and 6-membered rings having an oxygen atom, a sulphur atom, and/or up to 3 nitrogen atoms, are preferred. Those which may be mentioned as being particularly preferred are: pyrrolyl, pyrazolyl, pyridyl, pyrimidyl, pyrazinyl, pyridazinyl, thiazolyl, oxazolyl, imidazolyl, isoxazolyl, pyrrolidinyl, piperidinyl, piperazinyl, tetrazolyl or morpholinyl.

The compounds of the general formula (I) according to the invention possess, as the compound of the general formula

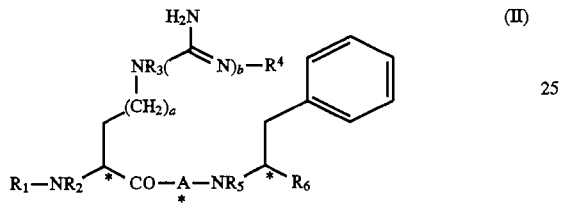 (II)

shows, at least 3 asymmetric carbon atoms (*). Independently of each other, they can be present in the D or L form and the R or S configuration. The invention includes the optical antipodes as well as the isomeric mixtures or racemates.

The compounds of the general formula (I) according to the invention can exist in stereoisomeric forms which for example either do (enantiomers) or do not (diastereomers) relate to each other as image and mirror image, or be present as a diastereomeric mixture. The invention relates to all of the antipodes, the racemic forms, the diastereomeric mixtures and the pure isomers. The racemic forms, like the diastereomeric mixtures, can be separated, in a known manner, into the stereoisomerically homogeneous constituents.

Separation into the stereoisomerically homogeneous compounds is effected, for example, by chromatographic racemate resolution of diastereomeric esters and amides, or on optically active phases. Crystallization of diastereomeric salts is also possible.

Compounds of the general formula (I) are preferred in which a represents a number 2 or 3, b represents a number 0 or 1, $R^1$ represents hydrogen, tert-butoxycarbonyl (Boc), benzyloxycarbonyl (Z), or 9-fluorenylmethoxycarbonyl (FMOC), or represents a radical of the formula $R^7-NR^8-CO-$, $R^9-(CH_2)_c-CO-$, $R^{10}-(CH_2)_d-O-CO$, or a radical of the formula $-SO_2-R^{11}$, in which $R^7$ denotes cyclopentyl or cyclohexyl, or straight-chain or branched alkyl having up to 16 carbon atoms which is optionally substituted by hydroxyl, methoxy, fluorine, chlorine, bromine, trifluoromethyl, trifluoromethoxy, cyclopentyl or cyclohexyl, or phenyl which, for its part, can be substituted identically or differently up to 2 times by carboxyl, cyano, hydroxyl, fluorine, chlorine, bromine or perhalogenoalkyl having up to 4 carbon atoms, or by straight-chain or branched acyl, alkoxy or alkoxy- carbonyl having in each case up to 4 carbon atoms, or alkyl is optionally substituted by a group of the formula $-CO_2R^{12}$, in which $R^{12}$ denotes hydrogen, or straight-chain or branched alkyl or alkenyl having in each case up to 6 carbon atoms which are optionally substituted by phenyl, or $R^7$ denotes phenyl, or naphthyl which is optionally substituted identically or differently up to 3 times by carboxyl, amino, fluorine, chlorine, bromine, hydroxyl, cyano or perhalogenoalkyl having up to 4 carbon atoms, or by straight-chain or branched acyl, alkoxy, vinylalkoxycarbonyl or alkoxycarbonyl having in each case up to 5 carbon atoms which, for its part, is substituted by straight-chain or branched alkoxy having up to 6 carbon atoms, or denotes an amino acid radical of the formula

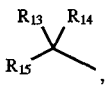

in which $R^{13}$ and $R^{14}$ are identical or different and denote hydrogen or methyl, or $R^{13}$ and $R^{14}$ together form a cyclopentyl or cyclohexyl ring, or $R^{13}$ denotes hydrogen or methyl, and $R^{14}$ denotes cyclopropyl, cyclopentyl, cyclohexyl, phenyl or hydrogen, or denotes straight-chain or branched alkyl having up to 6 carbon atoms, where the alkyl is optionally substituted by methylthio, hydroxyl, mercapto or guanidyl, or by a group of the formula $-NR^{16}R^{17}$ or $R^{18}-OC-$, in which $R^{16}$ and $R^{17}$, independently of each other, denote hydrogen, straight-chain or branched alkyl having up to 6 carbon atoms, or phenyl, and $R^{18}$ denotes hydroxyl, benzyloxy, alkoxy having up to 6 carbon atoms, or the above-listed group $-NR^{16}R^{17}$, or the alkyl is optionally substituted by cyclopropyl, cyclopentyl or cyclohexyl, or by phenyl which, for its part, is substituted by hydroxyl, fluorine, chlorine, bromine, nitro or alkoxy having up to 8 carbon atoms, or by the group $-NR^{16}R^{17}$, in which $R^{16}$ and $R_{17}$ have the abovementioned meaning, or the alkyl is optionally substituted by imidazolyl or indolyl in which the corresponding $-NH-$ functions are optionally protected by alkyl having up to 6 carbon atoms or by an aminoprotective group, $R^{15}$ denotes straight-chain or branched alkyl having up to 6 carbon atoms which is optionally substituted by hydroxyl or by straight-chain or branched alkoxy having up to 4 carbon atoms, or denotes carboxyl, allyloxycarbonyl, straight-chain or branched alkoxycarbonyl having up to 6 carbon atoms, or benzyloxycarbonyl, $R^7$ denotes a radical of the formula

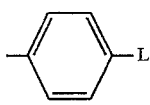

in which
L denotes phenyl or pyridyl $R^8$ denotes hydrogen, straight-chain or branched alkyl having up to 4 carbon atoms, tert-butoxycarbonyl (Boc) or benzyloxycarbonyl (Z), $R^9$ denotes straight-chain or branched alkyl having up to 6 carbon atoms, which is optionally substituted by pyridyl, or denotes phenoxy, phenyl, naphthyl, indolyl, quinolyl, quinoxalinyl, isoquinolyl, pyridyl, pyrazinyl, pyrimidyl, triazolyl or imidazolyl, where the cycles are optionally substituted identically or differently up to 3 times by nitro, carboxyl, cyano, hydroxyl, fluorine, chlorine, bromine or perhalogenoalkyl having up to 4 carbon atoms, or by straight-chain or branched alkyl, acyl, alkoxy or alkoxycarbonyl having in each case up to 4 carbon atoms, or phenyl is optionally substituted by pyridyl or triazolyl, where the latter two can in turn be substituted by phenyl, or $R^9$ denotes a radical of the formula

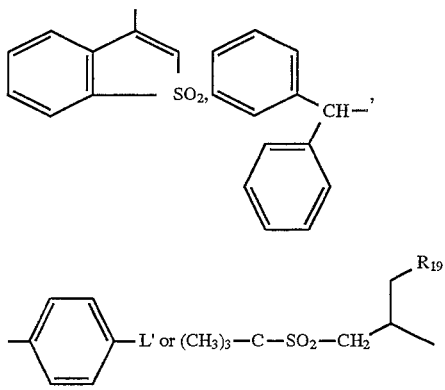

in which
L' has the abovementioned meaning of L and is identical to or different from the latter,
$R^{19}$ denotes phenyl or naphthyl,
c denotes a number 0, 1, 2 or 3,
d denotes a number 0, 1 or 2,
$R^{10}$ has the abovementioned meaning of $R^9$ and is identical to or different from the latter,
$R^{11}$ denotes methyl, or phenyl which is optionally substituted identically or differently up to 4 times by methyl or methoxy, or denotes a radical of the formula

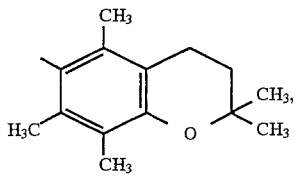

$R^2$, $R^3$ and $R^5$ are identical or different and denote Boc, hydrogen, methyl, ethyl, benzyloxycarbonyl or tert-butyl, $R^4$ represents hydrogen, nitro, benzyloxycarbonyl, tert-butoxycarbonyl or a radical of the formula $-SO_2R^{20}$, in which
$R^{20}$ has the abovementioned meaning of $R^{11}$ and is identical to or different from the latter, A represents a bond or a radical of the formula

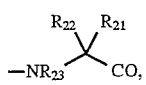

in which
$R^{21}$ and $R^{22}$ are identical or different and have the abovementioned meaning of $R^{13}$ and $R^{14}$ and are identical to or different from the latter,
$R^{23}$ has the abovementioned meaning of $R^2$, $R^3$ or $R^5$ and is identical to or different from the latter, $R^6$ represents formyl or carboxyl, or represents straight-chain or branched alkoxycarbonyl having up to 6 carbon atoms, or represents a radical of the formula $-CH_2-OR^{24}$ or $-CH(OR^{25})_2$, in which
$R^{24}$ and $R^{25}$ are identical or different and denote hydrogen, straight-chain or branched alkyl having up to 4 carbon atoms, acetyl or benzyl, and salts thereof, with the proviso that A must not represent valine.

Compounds of the general formula (I) are particularly preferred in which
a represents a number 2 or 3,
b represents a number 0 or 1,
$R^1$ represents hydrogen, tert-butoxycarbonyl (Boc) or benzyloxycarbonyl (Z), or represents a radical of the formula $R^7-NR^8-CO-$, $R^9-(CH_2)_c-CO-$, $R^{10}-(CH_2)_d-O-CO$, or represents a radical of the formula $-SO_2-R^{11}$, in which
$R^7$ denotes cyclopentyl or cyclohexyl, or straight-chain or branched alkyl having up to 14 carbon atoms which is optionally substituted by hydroxyl, methoxy, fluorine, trifluoromethyl, trifluoromethoxy or cyclohexyl, or phenyl which is optionally substituted by a group of the formula $-CO_2R^{12}$, in which
$R^{12}$ denotes hydrogen, or straight-chain or branched alkyl or alkenyl having in each case up to 4 carbon atoms, or benzyl, or
$R^7$ denotes phenyl which is optionally substituted identically or differently up to 3 times by carboxyl, fluorine, hydroxyl, cyano, trifluoromethyl or amino, or by straight-chain or branched acyl, alkoxy, vinylalkoxycarbonyl or alkoxycarbonyl having in each case up to 4 carbon atoms, which, for its part, is substituted by straight-chain or branched alkoxy having up to 4 carbon atoms, or denotes an amino acid radical of the formula

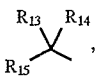

in which
$R^{13}$ and $R^{14}$ are identical or different and denote hydrogen or methyl, or
$R^{13}$ and $R^{14}$ together form a cyclopentyl or cyclohexyl ring, or
$R^{13}$ denotes hydrogen or methyl, and
$R^{14}$ denotes cyclopropyl, cyclopentyl, cyclohexyl, phenyl or hydrogen, or denotes straight-chain or branched alkyl having up to 6 carbon atoms, where the alkyl is optionally substituted by methylthio, hydroxyl, mercapto or guanidyl, or by a group of the formula —$NR^{16}R^{17}$ or $R^{18}$—OC—, in which $R^{16}$ and $R^{17}$, independently of each other, denote hydrogen, straight-chain or branched alkyl having up to 6 carbon atoms, or phenyl, and denotes hydroxyl, benzyloxy, alkoxy having up to 4 carbon atoms, or the above-listed group —$NR^{16}R^{17}$, or the alkyl is optionally substituted by cyclopropyl, cyclopentyl or cyclohexyl, or phenyl which, for its part, is substituted by hydroxyl, fluorine, chlorine, bromine, nitro, alkoxy having up to 6 carbon atoms, or by the group —$NR^{16}R^{17}$, in which $R^{16}$ and $R^{17}$ have the abovementioned meaning, or the alkyl is optionally substituted by imidazolyl or indolyl in which the corresponding —NH— functions are optionally protected by alkyl having up to 4 carbon atoms, tert-butoxycarbonyl or benzyloxycarbonyl, $R^{15}$ denotes straight-chain or branched alkyl having up to 4 carbon atoms which is optionally substituted by hydroxyl or straight-chain or branched alkoxy having up to 3 carbon atoms, or denotes carboxyl, allyloxycarbonyl, straight-chain or branched alkoxycarbonyl having up to 4 carbon atoms, or benzyloxycarbonyl, or $R^7$ denotes a radical of the formula

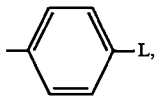

in which

L denotes phenyl or pyridyl, $R^8$ denotes hydrogen, methyl, ethyl or tert-butyl, $R^9$ denotes straight-chain or branched alkyl having up to 6 carbon atoms, which is optionally substituted by pyridyl, phenoxy, phenyl, naphthyl, indolyl, quinolyl, quinoxalinyl, isoquinolyl, pyridyl, pyrazinyl, pyrimidyl, triazolyl or imidazolyl, where the cycles are optionally substituted identically or differently up to 3 times by nitro, carboxyl, cyano, hydroxyl, fluorine, chlorine, bromine or perhalogenoalkyl having up to 4 carbon atoms, or by straight-chain or branched alkyl, acyl, alkoxy or alkoxycarbonyl having in each case up to 4 carbon atoms, or phenyl is optionally substituted by pyridyl or triazolyl, where the latter two can, in turn, be substituted by phenyl, or $R^9$ denotes a radical of the formula

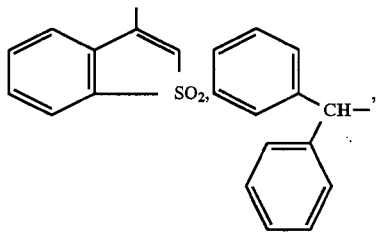

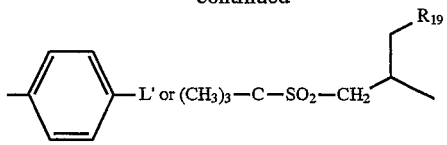

in which

L' has the abovementioned meaning of L and is identical to or different from the latter, $R^{19}$ denotes phenyl or naphthyl, c denotes a number 0, 1, 2 or 3, d denotes a number 0, 1 or 2, $R^{10}$ has the abovementioned meaning of $R^9$ and is identical to or different from the latter, $R^{11}$ denotes methyl, or phenyl which is optionally substituted identically or differently up to 4 times by methyl or methoxy, or denotes a radical of the formula

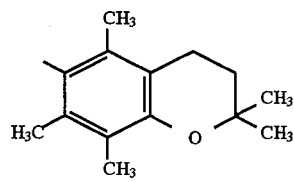

$R^2$, $R^3$ and $R^5$ are identical or different and denote Boc, hydrogen, methyl, ethyl, benzyloxycarbonyl or tertbutyl, $R^4$ represents hydrogen, nitro, benzyloxycarbonyl, tertbutoxycarbonyl, or represents a radical of the formula —$SO_2R^{20}$, in which $R^{20}$ has the abovementioned meaning of $R^{11}$ and is identical to or different from the latter, A represents a bond or a radical of the formula

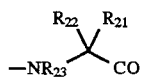

in which $R^{21}$ and $R^{22}$ are identical or different and have the abovementioned meaning of $R^{13}$ and $R^{14}$ and are identical to or different from the latter, $R^{23}$ has the abovementioned meaning of $R^2$, $R^3$ or $R^5$ and is identical to or different from the latter, $R^6$ represents formyl or carboxyl, or represents straight-chain or branched alkoxycarbonyl having up to 4 carbon atoms, or represents a radical of the formula —$CH_2$—$OR^{24}$ or —$CH(OR^{25})_2$, in which $R^{24}$ and $R^{25}$ are identical or different and denote hydrogen, straight-chain or branched alkyl having up to 3 carbon atoms, or benzyl, and salts thereof, with the proviso that A must not represent valine.

In addition, novel processes have been found for preparing the compounds of the general formula (I) according to the invention, which processes are characterized in that compounds of the general formula (III)

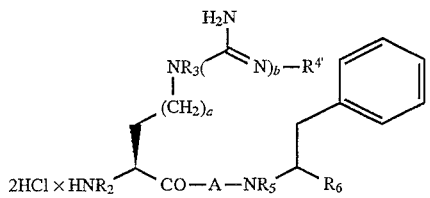

in which

A, a, b, $R^2$, $R^3$, $R^5$ and $R^6$ have the abovementioned meaning, and $R^{4'}$ has the abovementioned meaning of $R^4$, but does not represent hydrogen,

[A] in the case where $R^1$ represents the radical of the formula $R^7$—$NR^8$—CO—, are first converted, by reaction with compounds of the general formula (IV)

$$R^7-N=C=O \qquad (IV)$$

in which $R^7$ has the abovementioned meaning, in inert solvents and in the presence of a base, into the compounds of the general formula (V)

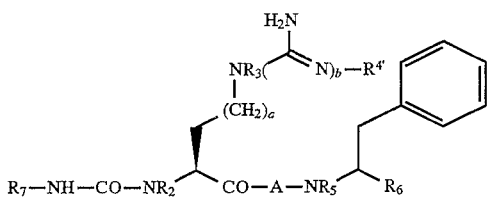

in which

A, a, b, $R^1$, $R^2$, $R^3$, $R^5$, $R^6$ and $R^7$ have the abovementioned meaning, or

[B] in the case where $R^1 \neq R^7$—NH—CO—, compounds of the general formula (III) are reacted with compounds of the general formula (VI) or (VII)

$$V-CO-W \qquad (VI)$$

or $$X-SO_2-R^{11} \qquad (VII)$$

in which $R^{11}$ has the abovementioned meaning,

V encompasses the above-listed scope of meaning of the radicals $R^9$—$(CH_2)_c$ or $R^{10}$—$(CH_2)_d$—O—, and W and X are identical or different and denote hydroxyl or a typical carboxylic-acid-activating radical, such as, for example, chlorine, in accordance with the methods which are customary in peptide chemistry, in inert organic solvents and in the presence of a base and an auxiliary substance, and, in the case where $R^2$, $R^3$, $R^5$ and $R^8 \neq H$, an alkylation in accordance with customary methods optionally follows, and, in the case where $R^6 = CH_2$—OH, the compounds of the general formula (V) ($R^6 = COOCH_3$) are reacted in accordance with customary methods, preferably, however, using sodium borohydride, and, in the case where $R^6 = CHO$, the compounds of the general formula (V), starting from the hydroxymethyl compound ($R^6 = CH_2$—OH), are subjected to an oxidation, depending on the radical $R^{4'}$, reaction takes place with hydrofluoric acid or trifluoroacetic acid, for example, to give $R^4 = H$, and, in the case of an aminoprotective group ($R^1$, $R^2$, $R^3$, $R^{4'}$ and $R^5$), this is eliminated in accordance with the methods which are customary in peptide chemistry, and, in the case of the acids, the esters are hydrolysed.

The process according to the invention can be illustrated, by way of example, by the following formula schemes (schemes 1–3):

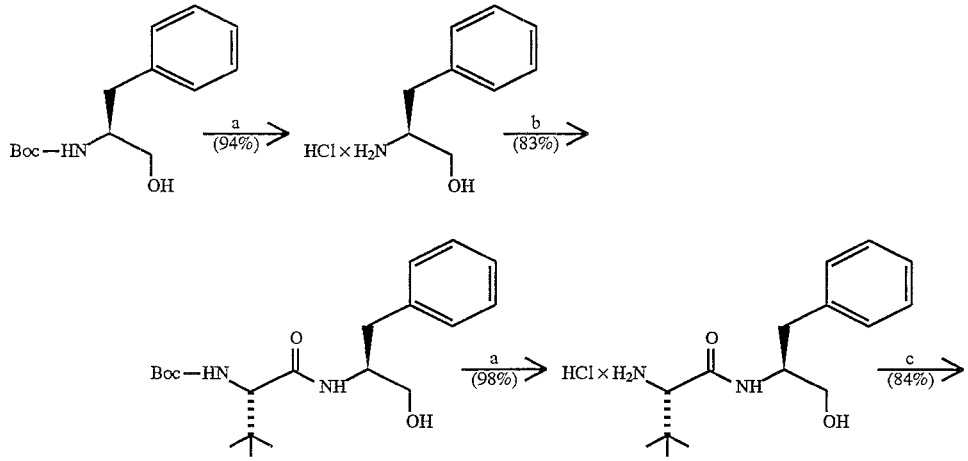

Scheme 1:
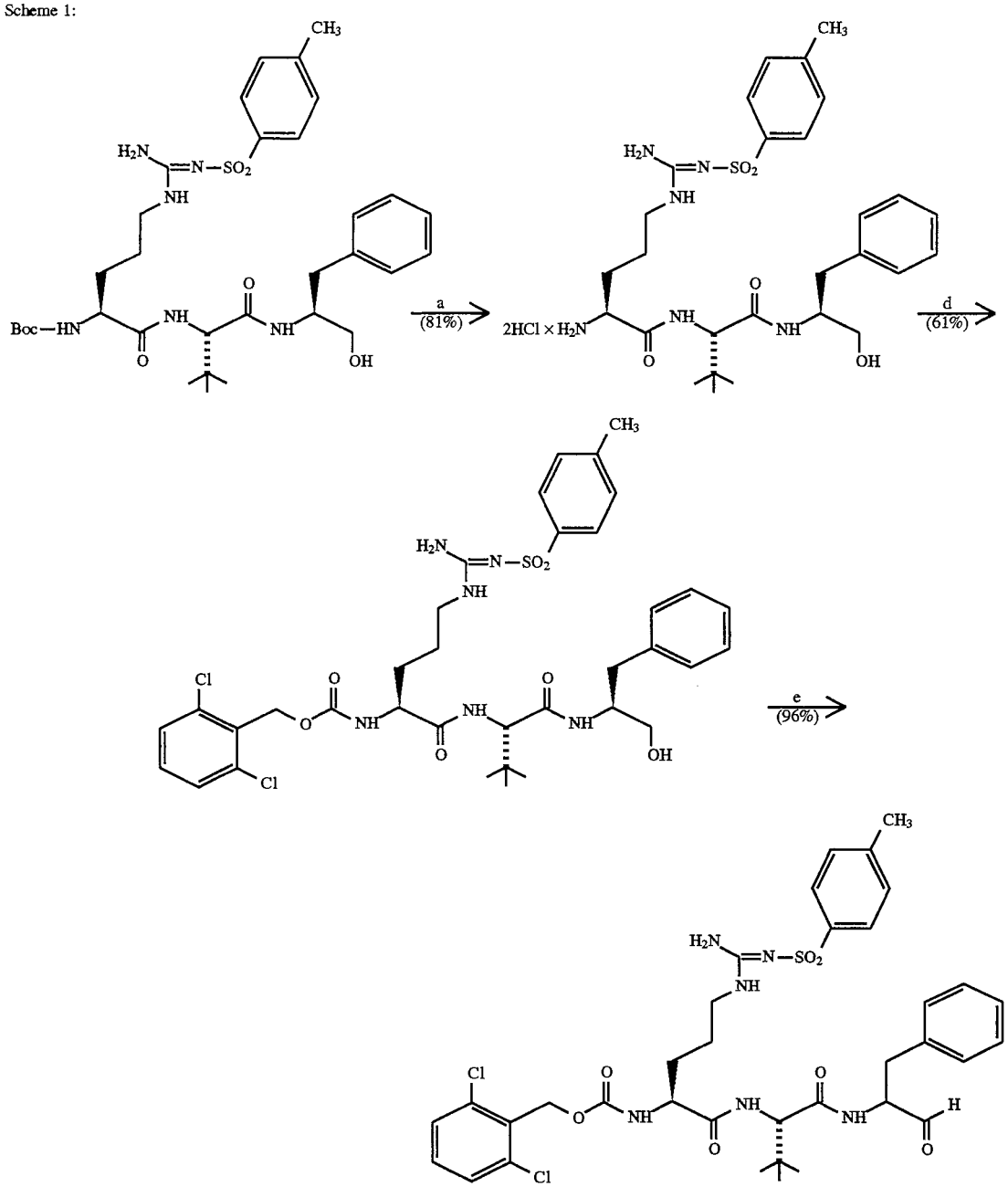
Reagents:
a) 4N HCl in dioxane; 30 min at room temperature
b) Boc-Gly(t-Bu)-OH, HOBT, DCC, CH$_2$Cl$_2$; 2 h at room temperature
c) Boc-Arg (Tos)-OH, HOBT, DCC, CH$_2$Cl$_2$/DMF; 1 h at room temperature
d) 2,6-Cl—C$_6$H$_3$—CH$_2$OCOCl, dioxane, water, pH 9–10, 2 h at room temperature
e) PyrxSO$_3$, NEt$_3$, DMSO, 1 h at room temperature
Scheme 2:
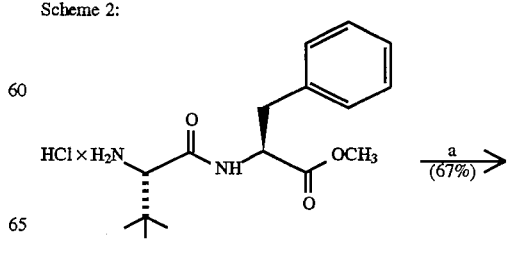

Scheme 2:
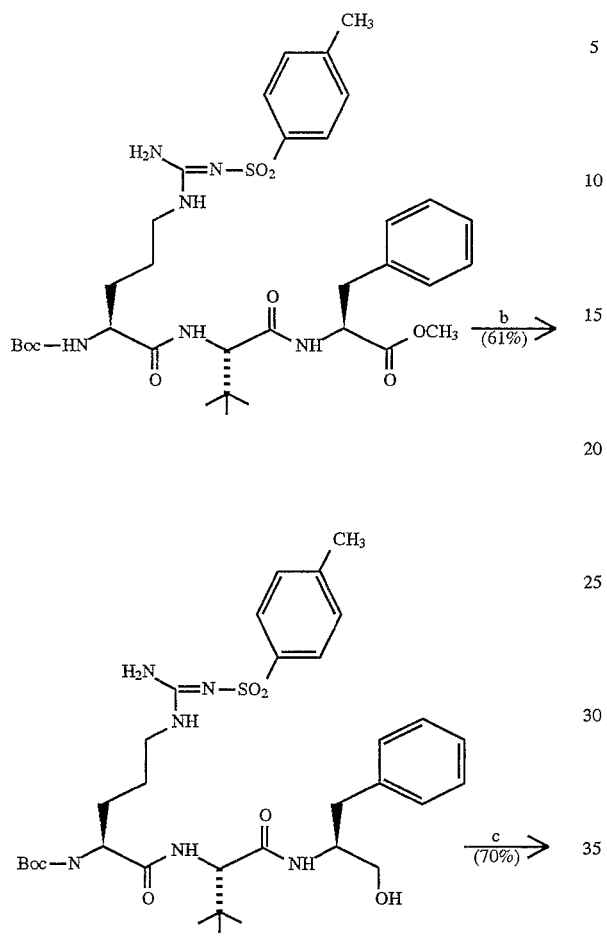
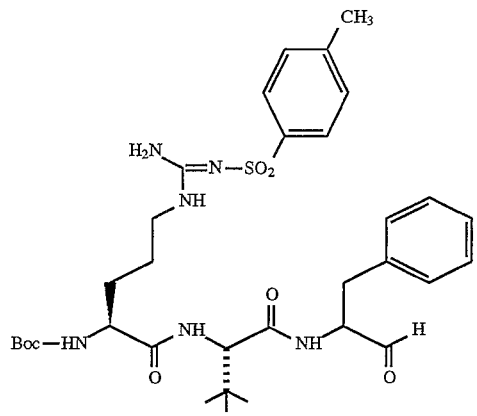
Reagents:
a) Boc-Arg(Tos)-OH, HOBT, DCC, CH$_2$Cl$_2$, DMF, 1 h at room temperature
b) NaBH$_4$, LiI, TBF, MeOH, 5 h at 40° C.
c) PyrxSO$_3$, NEt$_3$, DMSO, 1 h at room temperature
Scheme 3:
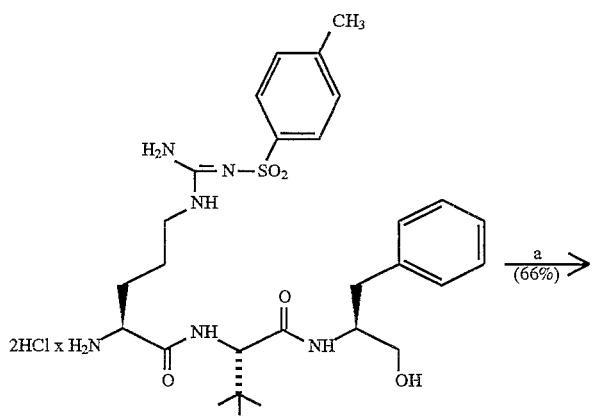

Scheme 3:

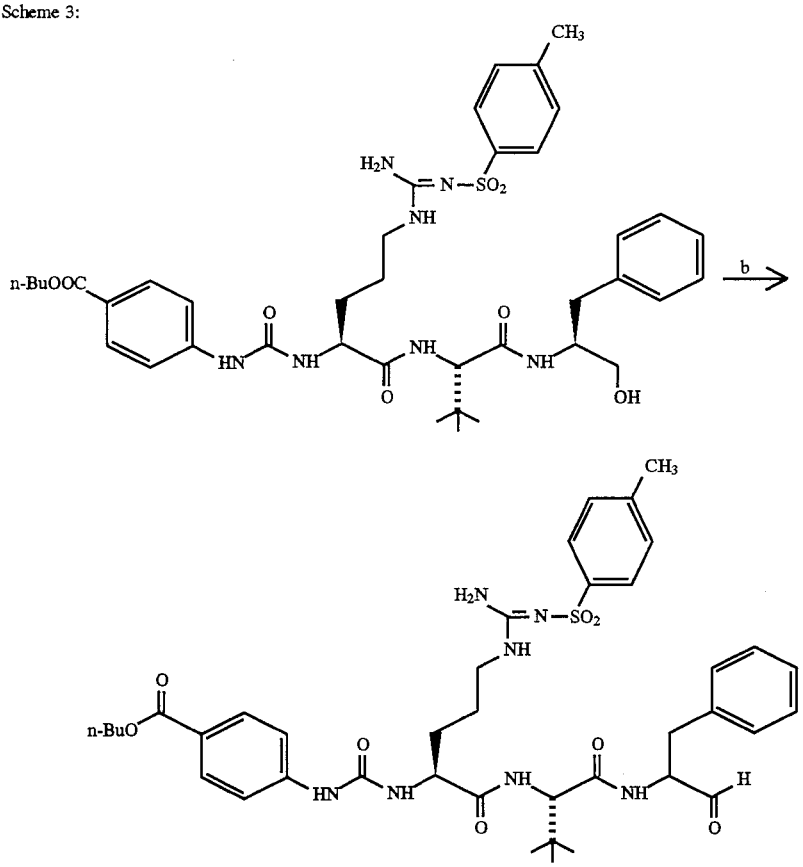

Reagents:
a) n-BuOCO—C₆H₄—NCO, NEt₃, CH₂Cl₂; 30 min at room temperature
b) PyrxSO₃, NEt₃, DMSO, 1 h at room temperature The customary inert solvents which are not altered under the reaction conditions are suitable for use as solvents for all procedural steps. These preferably include organic solvents, such as ethers, e.g. diethyl ether, glycol monomethyl ether, glycol dimethyl ether, dioxane or tetrahydrofuran, or hydrocarbons, such as benzene, p-cresol, toluene, xylene, cyclohexane or petroleum fractions, or halogenohydrocarbons, such as methylene chloride, chloroform or carbon tetrachloride, or dimethyl sulphoxide, dimethylformamide, hexamethylphosphoric triamide, ethyl acetate, pyridine, triethylamine or picoline. It is likewise possible to use mixtures of the said solvents, where appropriate together with water as well. Methylene chloride, tetrahydrofuran, dioxane and dioxane/water are particularly preferred.

Suitable bases are organic amines, trialkyl(C₁–C₆)amines, such as, for example, triethylamine, or heterocycles, such as pyridine, methylpiperidine, piperidine or N-methylmorpholine. Triethylamine and N-methylmorpholine are preferred.

The bases are generally employed in a quantity of 0.1 mol to 5 mol, preferably of 1 mol to 3 mol, in each case based on 1 mol of the compounds of the general formula (III), (VI) and (VII).

The reactions may be carried out under atmospheric pressure, and also at elevated or reduced pressure (e.g. 0.5 to 3 bar). In general, atmospheric pressure is employed.

The reactions are carried out in a temperature range from 0° C. to 100° C., preferably at 0° C. to 30° C., and under atmospheric pressure.

The aminoprotective groups are eliminated in a manner which is known per se.

In general, the tosyl group is eliminated using hydrofluoric acid (anhydrous) in the presence of a scavenger, preferably p-cresol, or using pyridinium hydrofluoride [see Matsuura et al., J. C. S. Chem. Comm. (1976), 451], in a temperature range from –10° C. to +30° C., preferably at 0° C.

Condensing agents, which can also be bases, are preferably employed as auxiliary substances for the respective peptide couplings, particularly if the carboxyl group is activated as an anhydride. Preferably, the customary condensing agents, such as carbodiimides, e.g. N,N'-diethylcarbodiimide, N,N'-dipropylcarbodiimide, N,N'-diisopropylcarbodiimide, N,N'-dicyclohexylcarbodiimide or N-(3-dimethylaminoisopropyl)-N'-ethylcarbodiimide hydrochloride, or carbonyl compounds, such as carbonyldiimidazole, or isoxazolium compounds, such as 2-ethyl-5-phenylisoxazolium-3-sulphonate or 2-tert-butyl-5-methylisoxazolium perchlorate, or acylamino compounds, such as 2-ethoxy-1-ethoxycarbonyl-1,2-dihydroquinoline, or propanephosphonic anhydride, or isobutyl chloroformate, or bis-(2-oxo-3-oxazolidinyl)-phosphoryl chloride, or benzotriazolyloxy-tri(dimethylamino)phosphonium hexafluorophosphate, or 1-hydroxybenzotriazole, and, as bases, alkali metal carbonates, e.g. sodium or potassium carbonate or sodium or potassium hydrogen carbonate, or organic bases, such as trialkyl amines, e.g. triethylamine, N-ethylmorpholine, N-methylpiperidine or diisopropylethylamine are employed for this purpose. Dicyclohexylcarbodiimide, N-methylmorpholine and 1-hydroxybenzotriazole are particularly preferred.

The carboxylic esters are hydrolysed in accordance with customary methods by treating the esters with customary bases in inert solvents, it being possible to convert the salts which first arise into the free carboxylic acids using an acid.

The customary inorganic bases can suitably be used for the hydrolysis. These bases preferably include alkali metal hydroxides or alkaline earth metal hydroxides, such as, for example, sodium hydroxide, lithium hydroxide, potassium hydroxide or barium hydroxide, or alkali metal carbonates, such as sodium or potassium carbonate or sodium hydrogen carbonate, or alkali metal alcoholates, such as sodium ethanolate, sodium methanolate, potassium ethanolate, potassium methanolate or potassium tertbutanolate. Sodium hydroxide or lithium hydroxide are particularly preferably employed.

Water, or the organic solvents which are customary for a hydrolysis, can suitably be employed as solvents for the hydrolysis. The organic solvents preferably include alcohols, such as methanol, ethanol, propanol, isopropanol or butanol, or ethers, such as tetrahydrofuran or dioxane, or dimethylformamide or dimethyl sulphoxide. Alcohols such as methanol, ethanol, propanol or isopropanol are particularly preferably used. It is likewise possible to employ mixtures of the said solvents. Water/tetrahydrofuran is preferred.

In general, the hydrolysis is carried out in a temperature range from 0° C. to +100° C., preferably from 0° C. to +40° C.

In general, the hydrolysis is carried out under atmospheric pressure. However, it is also possible to carry it out under reduced pressure or under excess pressure (e.g. from 0.5 to 5 bar).

When carrying out the hydrolysis, the base or the acid is generally employed in a quantity of 1 to 3 mol, preferably of 1 to 1.5 mol, based on 1 mol of the ester. Molar quantities of the reactants are particularly preferably used.

When carrying out the reaction, the salts of the compounds according to the invention arise in the first step as intermediates which can be isolated. The acids according to the invention are obtained by treating the salts with customary inorganic acids. These preferably include mineral acids, such as, for example, hydrochloric acid, hydrobromic acid, sulphuric acid, citric acid or phosphoric acid. When preparing the carboxylic acids, it has been found to be advantageous to acidify the basic reaction mixture of the hydrolysis in a second step without isolating the salts. The acids may then be isolated in a customary manner.

In general, the reductions can be carried out by hydrogen in water or in inert organic solvents, such as alcohols, ethers or halogenohydrocarbons, or their mixtures, using catalysts such as Raney nickel, palladium, palladium on animal charcoal or platinum, or using hydrides or boranes in inert solvents, where appropriate in the presence of a catalyst.

Preferably, the reduction is carried out using hydrides, such as complex borohydrides or aluminium hydrides. In this context, sodium borohydride, lithium aluminium hydride or sodium cyanoborohydride are particularly preferably employed.

In this context, all inert organic solvents which are not altered under the reaction conditions are suitable for use as solvents. These preferably include alcohols, such as methanol, ethanol, propanol or isopropanol, or ethers, such as diethyl ether, dioxane, tetrahydrofuran, glycol dimethyl ether, or diethylene glycol dimethyl ether, or amides, such as hexamethylphosphoric triamide or dimethylformamide, or acetic acid. It is likewise possible to use mixtures of the said solvent. Methanol and tetrahydrofuran are preferred.

Potassium or lithium iodide, preferably lithium iodide, may be employed as catalysts in the reductions.

The catalyst is generally employed in a quantity of 0.1 mol to 5 mol, preferably of 1 mol to 3 mol, in each case based on 1 mol of the ester to be reduced.

The reaction can be carried out under atmospheric, elevated or reduced pressure (e.g. 0.5 to 5 bar). In general, atmospheric pressure is employed.

In general, the reductions are carried out in a temperature range from 0° C. to +60° C., preferably at +10° C. to 40° C.

The oxidation of alcohol groups to give the corresponding aldehydes is generally effected in one of the above-listed solvents, in the presence of one of the above-listed bases, using oxidizing agents, such as, for example, potassium permanganate, bromine, Jones reagent, pyridinium dichromate, pyridiniumchlorochromate, pyridine sulphur trioxide complex, or using sodium hypochlorite and 2,2,6, 6-tetramethylpiperidinyloxy (TEMPO) [Org. Synth. 69, 212 (1990)] or oxalyl chloride [Swern-Oxidation (ClCOCOCl/ DMSO/CH$_2$Cl$_2$/NEt$_3$), e.g. in accordance with R. E. Ireland et al., J. Org. Chem. 50, 2199 (1985)]. Preferably, the oxidation is effected using pyridine sulphur trioxide complex in dimethyl sulphoxide in the presence of triethylamine.

In general, the oxidation is effected in a temperature range from 0° C. to +50° C., preferably at room temerature and under atmospheric pressure.

The alkylation is carried out in the above-listed solvents at temperatures of 0° C. to +150° C., preferably at +20° C. to +100° C., under atmospheric pressure.

Customary organic solvents which are not altered under the reaction conditions may likewise suitably be used as solvents for the alkylation. These solvents preferably include ethers, such as diethyl ether, dioxane, tetrahydrofuran or glycol dimethyl ether, or hydrocarbons, such as benzene, toluene, xylene, hexane, cyclohexane or petroleum fractions, or halogenohydrocarbons, such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoric triamide, acetonitrile, acetone or nitromethane. It is likewise possible to use mixtures of the said solvents. Dimethylformamide is preferred. Sodium hydride can also be employed as a base in the alkylation.

The compounds of the general formula (III) are for the most part novel and can be prepared in accordance with the methods which are customary in peptide chemistry, by, for example, reacting compounds of the general formula (VIII)

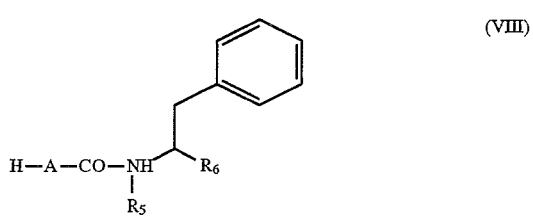

(VIII)

in which $R^5$, $R^6$ and A have the abovementioned meaning, with the amino acid derivatives of the formula (IX)

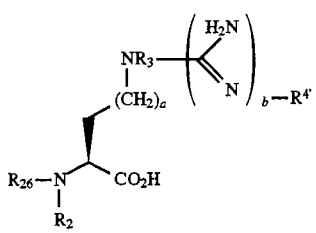

(IX)

in which a, b, $R^2$, $R^3$ and $R^{4'}$ have the abovementioned meaning, and $R^{26}$ represents one of the above-listed amino protective groups, preferably 9 fluorenylmethoxycarbonyl, (Fmoc), tert-butoxycarbonyl (Boc) or Benzyloxycarbonyl (Z), in one of the abovementioned solvents, preferably methylene chloride, in the presence of an auxiliary substance and/or base, preferably HOBT and dicyclohexylcarbodiimide, and, subsequently, likewise in accordance with customary methods, eliminating the aminoprotective group, and especially, for preference, eliminating Boc with hydrochloric acid in dioxane, Fmoc with piperidine, and Z with HBr/HOAc or by hydrogenolysis.

All procedural steps are effected under atmospheric pressure and in a temperature range of 0° C. to room temperature, preferably at room temperature.

The compounds of the general formulae (VIII) and (IX) are for the most part known, or can be prepared in accordance with customary methods [cf. J. Chem. Res., Synop., (S), 62–63; DE 36 04 510].

The compounds of the general formula (V) are likewise known [cf. U.S. Pat. No. 4,929,736].

The compounds of the general formulae (VI) and (VII) are known.

The compounds demonstrate an antiviral effect towards retroviruses and representatives of the Herpetoviridae group, particularly towards human cytomegalovirus (HCMV).

The anti-HCMV effect was determined in a screening test system in 96-well microtitre plates, making use of human embryonic lung fibroblasts (HELF) cell cultures. The influence of the substances on the spread of the cytopathogenic effect was compared with that of the reference substance ganciclovir (Cymevene® sodium), a clinically approved anti-HCMV chemotherapeutic agent.

The substances dissolved in DMSO (dimethyl sulphoxide) (at 50 mM concentration) are investigated on microtitre plates (96-well) at final concentrations of 1,000–0.00048 µM (micromolar) in double determinations (4 substances/plate). The conditions are such that both toxic and cytostatic effects of the substances are recorded. Once the appropriate substance dilutions (1:2) have been made on the microtitre plate, a suspension of 50–100 HCMV-infected HELF cells and 3×10⁴ non-infected HELF cells in Eagle's MEM (minimal essential medium) containing 10% foetal calf serum is added to each well and the plates are then incubated at 37° C. in a $CO_2$ incubator for a period of 6 days. At the end of this time, the cell lawn in the substance-free virus controls is, starting from 50–100 infectious centres, completely destroyed by the cytopathogenic effect (CPE) of the HCMV (100% CPE). After staining with neutral red and fixing with formalin/methanol, the plates are evaluated with the aid of a projection microscope (plaque viewer). The results for some of the compounds are summarized in the following table:

TABLE

Anti-HCMV (Davis) activity and anti-cellular effect

| Ex. No. | $CIC_{50}$ (µM)[1] (HELF) | $IC_{50}$ (µM)[2] (HCMV) | SI[3] |
|---|---|---|---|
| 22 | 62.5 | 1.95 | 32 |
| 50 | 2.8 | 0.004 | 700 |
| 52 | 15.6 | 0.125 | 125 |
| 62 | 14.3 | 0.163 | 88 |
| 63 | 93.8 | 0.49 | 191 |
| 67 | 23.4 | 0.214 | 109 |
| 68 | 344 | 4.9 | 70 |
| 69 | 2.6 | 0.013 | 200 |
| 70 | 51 | 0.98 | 52 |
| 71 | 187.5 | 0.98 | 191 |
| 72 | 3.44 | 0.023 | 150 |
| 73 | 0.56 | 0.0013 | 430 |
| 74 | 7.8 | 0.046 | 170 |
| 75 | 0.86 | <0.0005 | 1,720 |
| 77 | 9.8 | 0.061 | 160 |
| 83 | 62.5 | 0.244 | 256 |
| Cymevene.Na | 125 | 2–4 | 32–64 |

[1] $CIC_{50}$ = Highest concentration which does not show any obvious anti-cellular effect.
[2] $IC_{50}$ = Concentration of the compound according to the invention which causes 50% inhibition of the CPE
[3] $SI = \dfrac{CIC_{50}}{IC_{50}}$ = selectivity index It has now been found that the compounds according to the invention inhibit replication of HCMV in HELF cells in concentrations which are in some cases 10–50 times lower than those of Cymevene® sodium, and have a selectivity index which is several times higher.

The compounds according to the invention thus represent valuable active compounds for the treatment and prophylaxis of diseases caused by human cytomegalovirus. Indications which may be mentioned by way of example are:

1) Treatment and prophylaxis of cytomegalovirus infections in patients who are undergoing bone marrow and organ transplantations and who often contract life-threatening HCMV pneumonitis and encephalitis and gastrointestinal and systemic HCMV infections.

2) Treatment and prophylaxis of HCMV infections in AIDS patients (retinitis, pneumonitis and gastrointestinal infections).

3) Treatment and prophylaxis of HCMV infections in pregnant women, the newborn and small children.

Over and above this, it was found, surprisingly, that the compounds of the general formula (I) possess an effect against retroviruses. This is verified using an HIV-specific protease enzyme test.

The results of the examples listed below were obtained using the HIV test system described in the following literature reference [cf. Hansen, J., Billich, S., Schulze, T., Sukrow, S. and M ölling, K. (1988), EMBO Journal, Vol, 7, No. 6, pp. 1785–1791]: purified HIV protease was incubated with synthetic peptide which imitates a cleavage site in the gag precursor protein and represents an in-vivo cleavage site for HIV protease. The cleavage products resulting from the synthetic peptide were analysed by reverse phase high performance liquid chromatography (RP-HPLC). The $IC_{50}$ values which are given relate to that concentration of substance which brings about 50% inhibition of the protease activity under the above-listed test conditions.

TABLE

| Ex. No. | IC$_{50}$ (RP-HPLC) (μM) HIV-1 |
|---|---|
| 43 | 2.6 |
| 47 | 13 |
| 52 | 1.9 |
| 71 | 0.21 |
| 80 | 19 |

The novel active compound can, in a known manner, be converted into the customary formulations, such as tablets, coated tablets, pills, granules, aerosols, syrups, emulsions, suspensions and solutions, using inert, non-toxic, pharmaceutically suitable excipients or solvents. In this context, the therapeutically active compound should in each case be present at a concentration of about 0.5 to 90% by weight of the total mixture, i.e. in quantities which are adequate to achieve the given dosage scope.

The formulations are prepared, for example, by extending the active compounds with solvents and/or excipients, where appropriate using emulsifiers and/or dispersing agents, it being possible, for example when using water as a diluent, to use organic solvents as solubilizers where appropriate.

Administration is effected in a customary manner, preferably orally, parenterally or topically, especially perlingually or intravenously.

For parenteral applications, solutions of the active compound can be employed which make use of suitable liquid carrier materials.

In general, it has been found to be advantageous to administer quantities of about 0.001 to 10 mg/kg, preferably about 0.01 to 5 mg/kg, of body weight to achieve effective results in the case of intravenous administration, and, in the case of oral administration, the dosage is about 0.01 to 25 mg/kg, preferably 0.1 to 10 mg/kg, of body weight.

Despite this, it can be necessary, where appropriate, to diverge from the said quantities, specifically depending on the body weight and the nature of the route of administration, on the individual response to the medicament, on the nature of its formulation, and on the time point or interval at which the administration is effected. Thus it can, in some cases, be adequate to make do with less than the aforementioned lowest quantity, while, in other cases, the said upper limit must be exceeded. When larger quantities are being administered, it can be advisable to divide these into several smaller doses which are administered over the course of the day.

As enzyme inhibitors, the compounds according to the invention may be employed in all areas which are generally known as being suitable for inhibitors. This means, for example, their employment as affinity labels in affinity chromatography used for purifying proteases. They can, as well, serve as aids for elucidating enzyme reaction mechanisms and for improving the specificity of diagnostic methods.

Appendix to the experimental section
I. Amino acids

In general, the configuration is designated by placing an L or D in front of the amino acid abbreviation, and in the case of the racemate by a D,L-, although, for simplicity, the configuration designation can be omitted in the case of L-amino acids, with a more explicit designation then only being given in the case of the D form or the D,L mixture.

| Ala | L-alanine |
| Arg | L-arginine |
| Ile | L-isoleucine |
| Leu | L-leucine |
| Phe | L-phenylalanine |
| Gly | glycine |
| Orn | L-ornithine |
| Lys | L-lysine |

—Gly(t-Bu)— 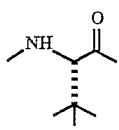

—NCH$_3$—Ile— 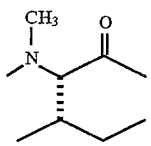

—NCH$_3$—Ala— 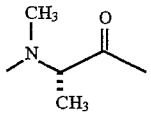

—NCH$_3$—Gly— 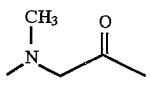

—βAla— 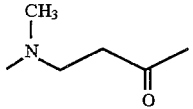

—Aib— 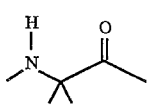

—Arg(Tos)— 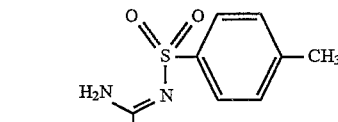 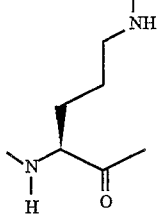

—Arg(NO₂)—

—Lys(Tos)—

—Orn(Z)—

II. Abbreviations
Z benzyloxycarbonyl
Boc tert-butyloxycarbonyl
CMCT 1-cyclohexyl-3-(2-morpholino-ethyl)-carbodiimide metho-p-toluenesulphonate
DCC dicyclohexylcarbodiimide
DMF dimethylformamide
HOBT 1-hydroxybenzotriazole
Ph phenyl
THF tetrahydrofuran
DMSO dimethyl sulphoxide
Fmoc 9-fluorenylmethoxycarbonyl
III. List of the eluent mixtures used for the chromatography
I: Dichloromethane:methanol
II: Toluene:ethyl acetate
III: Acetonitrile:water
Starting compounds

EXAMPLE I (2S)-2-Amino-3-phenyl-propan-1-ol hydrochloride

A solution of 20.10 g (80.00 mmol) of (S)-2-(tert-butoxycarbonylamino-1-phenyl-propan-1-ol [J. Med. Chem. 33, 2707 (1990)] in 200 ml of a 4N solution of gaseous hydrogen chloride in anhydrous dioxane is stirred at room temperature for 30 min. After that, 60 ml of toluene are added and the mixture is concentrated in vacuo. This procedure is repeated a further two times and the residue is then triturated with a little ether, filtered off with suction and dried under high vacuum over KOH. 14.14 g (94% of theory) of the title compound are obtained as colourless crystals.

m.p.: 148°–150° C. (ether) $R_f$=0.25 (acetonitrile:water 9:1) MS(DCI, NH₃) m/z=152 (M+H)⁺

IR(KBr) 3357, 2928, 1571, 1495, 1456, 1026, 738, 708 cm⁻¹ $[\alpha]^{20}_D$=4.2° (c=2.94, CH₃OH)

¹H-NMR (300 MHz, CD₃OD) δ=2.95 (d, 2H, J=7.5 Hz, CH₂); 3.50 (m, 2H); 3.70 (m, 1H); 7.30 (m, 5H, Ph). C₉H₁₃NO×HCl (187.67)

EXAMPLE II (2S)-2-[N-(tert-Butoxycarbonyl)-S-(tert-butyl) glycinyl]-amino-3-phenyl-propan-1-ol 21.70 g (105.00 mmol) of DCC are added to a solution, which is cooled to 0° C. and stirred, of 25.44 g (110.00 mmol) of N-(tert-butoxycarbonyl)-S-(tertbutyl)glycine and 16.85 g (110.00 mmol) of HOBT in 300 ml of anhydrous dichloromethane, and the mixture is then stirred for 5 min. After that, a solution of 18.80 g (100.00 mmol) of the compound from Example I and 38.50 ml (350.00 mmol) of N-methylmorpholine in 300 ml of dichloromethane is added dropwise. The cooling bath is removed and the reaction mixture is left to stir for 12 h at room temperature. The end of the reaction is established by thin layer chromatography. The urea which has arisen is separated off by filtration and the filtrate is concentrated in vacuo and the crude product purified by chromatography on 450 g of silica gel (dichloromethane:methanol 95:5). 30.23 g (83% of theory) of the title compound are obtained as colourless crystals.

m.p.: 188° C. $R_f$=0.23, I (95:5)

MS(FAB): m/z=(M+H)⁺365

The compounds listed in Table I were obtained, as described for Example II, by condensing the compound from Example I with the corresponding N- protected amino acids:

TABLE I

| Ex. No. | R⁹ | Yield (% of theory) | MS (FAB) m/z (M + H)⁺ | R_f/ eluent ratio | M.p. (°C.) |
|---|---|---|---|---|---|
| III | Fmoc-N(CH₃)-CH(iBu)- | 57 | 501 | 0.31, I (95:5) | Oil |
| IV | Boc-NH-CH(iBu)- | 83 | 365 | 0.50, I (9:1) | 133 |
| V | Boc-N(CH₃)-CH(CH₃)-CH₃ | 97 | 337 | 0.42, I (9:1) | 98 |
| VI | Boc-N(CH₃)-CH₂CH₂CH₃ | 86 | 323 | 0.40, I (9:1) | foam |
| VII | Boc-NH-CH₂CH₂CH₃ | 87 | 323 | 0.31, I (9:1) | amorphous |
| VIII | Boc-NH-C(CH₃)₃ | 86 | 337 | 0.21, I (9:1) | 79 |

EXAMPLE IX (2S)-2-[S-(tert-Butyl)glycinyl]amino-3-phenyl-propan-1-ol

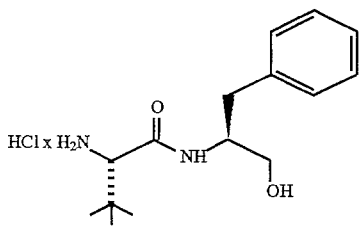

60 ml of a 4N solution of gaseous hydrogen chloride in anhydrous dioxane are added to a solution of 12.90 g (35.40 mmol) of the compound from Example II in 60 ml of anhydrous dioxane, and the mixture is stirred at room temperature for 30 min. After that, 60 ml of toluene are added and the mixture is concentrated in vacuo. This procedure is repeated a further 2 times and the residue is then triturated with 200 ml of ether, filtered off with suction and dried under high vacuum over KOH. 10.45 g (98% of theory) of the title compound are obtained as colourless crystals.

m.p.: from 105° C. (decomp.) $R_f$=0.20, III (95:5)

MS(FAB): m/z=265 (M+H)⁺

The hydrochlorides listed in Table II are obtained, as described for Example IX, after eliminating the amino-protective groups from the compounds described in Table I:

TABLE II

HCl × R9—CO—NH—CH(CH₂Ph)—CH₂OH

| Ex. No. | R⁹ | Yield (% of theory) | MS (FAB) m/z (M + H)⁺ | R_f/ eluent ratio | m.p. (°C.) |
|---|---|---|---|---|---|
| X | HN(CH₃)-CH(CH₃)(CH₃)- | 77 | 279 | 0.19, I (9:1) | 90 |
| XI | H₂N-C(CH₃)(CH₃)- | 98 | 265 | 0.43, III (9:1) | 126 |
| XII | HN(CH₃)-CH(CH₃)- | 87 | 237 | 0.05, I (85:5) | 164 |
| XIII | HN(CH₃)-CH₂CH₃ | 96 | 223 | 0.05, I (85:15) | 177 |
| XIV | H₂N-CH₂-CH₂- | 92 | 223 | 0.05, I (85:15) | 127 |
| XV | H-NH-C(CH₃)₃ | 78 | 237 | 0.10, I (8:2) | 107 |

¹⁾free base, obtained by eliminating the Fmoc group with piperidine

Preparation examples

Example 1

(2S)-2-[Nα-(tert-Butoxycarbonyl)-N^G-(4-methyl-phenylsulphonyl)-S-arginyl-S-tert-butyl-glycinyl] amino-3-phenylpropan-1-ol

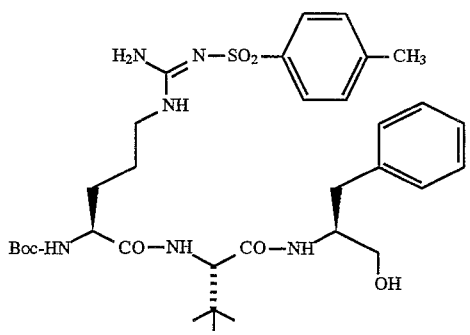

Method A:

7.92 g (38.39 mmol) of DCC are added to a solution, which is cooled to 0° C. and stirred, of 15.67 g (36.56 mmol) of N_a-(tert-butoxycarbonyl)-N^G-(4-methylphenylsulphonyl) -S-arginine and 6.16 g (40.22 mmol) of HOBT in 120 ml of anhydrous dichloromethane and 12 ml of DMF, and the mixture is stirred for 5 min. After that, a solution of 10.00 g (33.24 mmol) of the compound from Example IX and 14.60 ml (133.00 mmol) of N-methylmorpholine in 70 ml of dichloromethane and 7 ml of DMF is added dropwise. The cooling bath is removed and the reaction mixture is left to stir at room temperature for 1 h. The end of the reaction is established by thin layer chromatography. The urea which has arisen is separated off by filtration and the filtrate is concentrated in vacuo and the crude product purified by chromatography on 500 g of silica gel (dichloromethane:methanol 9:1). 18.95 g (84% of theory) of the title compound are obtained as a colourless foam.

MS(FAB): m/z (M+H)$^+$=675 R$_f$=0.14 (dichloromethane:methanol 9:1)

Method B:

16.87 g (24.00 mmol) of the compound from Example 3 are added in portions, within the space of 10 min, to a solution, which is stirred and heated at 40° C., of 1.36 g (36.00 mmol) of sodium borohydride and 4.83 g (36.00 mmol) of lithium iodide in 90 ml of THF. 25 ml of methanol are added slowly dropwise, at 40° C., to this mixture within the space of 5 h. The end of the reaction is established by thin layer chromatography and the reaction mixture is then poured into 250 ml of a dilute solution of citric acid. The mixture is then extracted four times with 50 ml of ethyl acetate on each occasion and the combined extracts are dried over MgSO$_4$. After evaporating off the solvent in vacuo, and after chromatography of the residue on 450 g of silica gel (dichloromethane:methanol 9:1), 9.90 g (61%) of the title compound are obtained.

Example 2

(2S)-2-[N$^G$-(4-Methyl-phenylsulphonyl)-S-arginyl-S-tertbutyl-glycinyl]amino-3-phenyl-propan-1-ol dihydrochloride

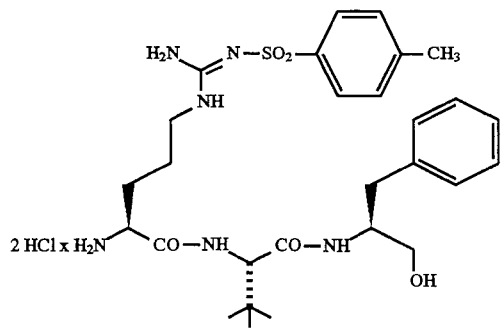

As described for Example I, 13.51 g (81% of theory) of the title compound are obtained as a colourless powder from 18.50 g (27.41 mmol) of the compound from Example I.

m.p.: 186° C. (decomp.) R$_f$=0.34 (dichloromethane:methanol 85:15)

MS(FAB): m/z=575 (M+H)$^+$

Example 3

Nα-(tert-Butoxycarbonyl)-N$^{GO}$-(4-methyl-phenylsulphonyl)-S-arginyl-S-tert-butyl-glycinyl-S-phenylalanine methyl ester

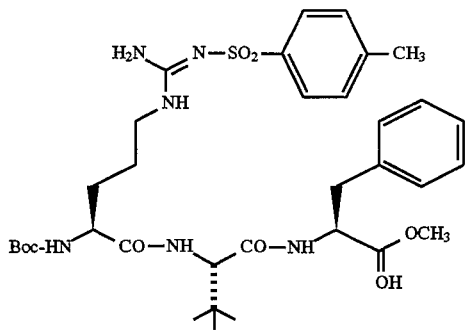

As described for Example I (method A), 4.55 g (67% of theory) of the title compound are obtained as an amorphous powder from 4.71 g (11.00 mmol) of Nα-(tertbutoxycarbonyl)-N$^G$-(4-methyl-phenylsulphonyl)-S-arginine and 3.15 g (9.57 mmol) of S-(tert-butyl)glycine-S-phenylalanine methyl ester hydrochloride after 4 h at room temperature.

R$_f$=0.35 (ethyl acetate)

MS(FAB): m/z=703 (M+H)$^+$

Example 4

N$^G$-(4-Methyl-phenylsulphonyl)-S-arginyl-S-tert-butylglycinyl-S-phenylalanine methyl ester dihydrochloride

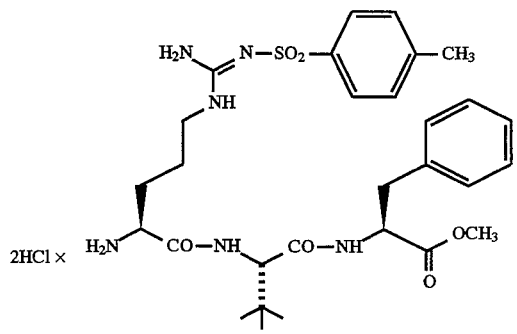

As described for Example I, 3.18 g (86% of theory) of the title compound are obtained as a colourless powder from 3.85 g (5.50 mmol) of the compound from Example 3.

m.p.: from 163° C. (decomp.) R$_f$=0.22 (dichloromethane:methanol 9:1)

Example 5

Nα-(tert-Butoxycarbonyl)-N^G-(4-methyl-phenyl-sulphonyl)-S-arginyl-S-tert-butyl-glycinyl-S-phenylalanine

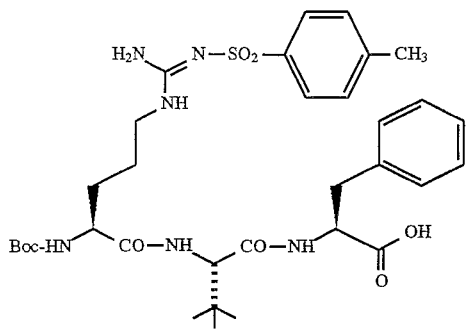

91 mg (2.00 mmol) of lithium hydroxide hydrate are added to a solution of 703 mg (1.00 mmol) of the compound from Example 3 in 6 ml of THF and 8 ml of water, and the mixture is then stirred at room temperature for 30 min. After that, the reaction mixture is poured into 40 ml of ethyl acetate. The organic phase is separated off and the aqueous phase is extracted once again with 10 ml of ethyl acetate. The aqueous phase is freed of solvent residues on a rotary evaporator and then adjusted to pH 5.2 with 0.5N hydrochloric acid. The resultant precipitate is thoroughly stirred for 10 min, separated off by filtration, and then dried under high vacuum initially over KOH and then over Sicapent. 412 mg (60%) of the title compound are obtained as an amorphous powder.

m.p.: 72° C. (decomp.) $R_f$=0.23 (acetonitrile:water=9:1) MS(FAB): m/z=689 (M+H)$^+$ The compounds described in Table I are obtained, as described for Example 1, by condensing the amines from Table II with different protected amino acids:

Example 11

(2S)-2-[Nα-(tert-Butoxycarbonyl)-N^G-(4-methyl-phenylsulphonyl)-S-arginyl-(S)-(N-methyl)-isoleucinyl]amino-S-phenyl-propan-1-ol

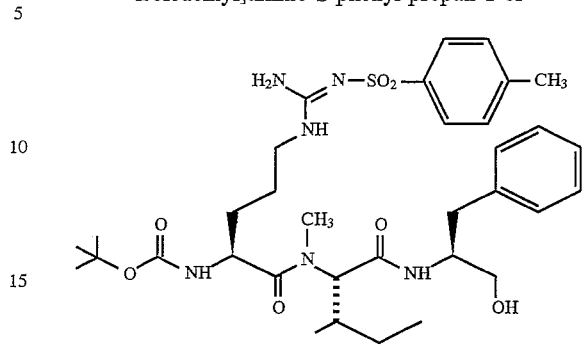

603 mg (2.37 mmol) of bis-(2-oxo-3-oxazolidinyl)-phosphoryl chloride are added to a suspension, which is stirred and cooled at −10° C. of 600 mg (2.16 mmol) of the compound from Example X and 926 mg (2.16 mmol) of Nα-(tert-butoxycarbonyl)-N^G-(4-methylphenylsulphonyl)-S-arginine in 10 ml of anhydrous dichloromethane, upon which a clear solution is obtained. After that, 1.33 ml (7.63 mmol) of ethyl-diisopropylamine are added, and the reaction mixture is subsequently stirred at −10° C. for 2 h and then poured into 60 ml of 1N NaHCO$_3$ solution. The organic phase is separated off and the water phase is extracted with 20 ml of dichloromethane. The combined organic extracts are washed with 50 ml of water and dried over MgSO$_4$. After evaporating off the solvent in vacuo, and chromatography of the residue on 42 g of silica gel (dichloromethane:methanol 9:1), 692 mg (47%) of the title compound are obtained as a pale foam.

$R_f$=0.25 (dichloromethane:methanol 9:1) MS(FAB): m/z=689 (M+H)$^+$

The products listed in Table 2 are obtained, as described for Example 11, by coupling the compounds from Table II

TABLE 1

Y—A—NH—CH(CH$_2$Ph)—CH$_2$OH

| Ex. No. | Y | A | Yield (% of theory) | MS (FAB) m/z (M + H)$^+$ | $R_f$/eluent ratio | M.p. (°C.) |
|---|---|---|---|---|---|---|
| 6 | Boc—Arg(Tos)— | — | 97 | 562 | 0.09, I (9:1) | foam |
| 7 | Boc—Arg(Tos)— | —Gly(t-Bu)— | 84 | 675 | 0.14, I (9:1) | amorphous |
| 8 | Z—Arg(Tos)— | —Gly(t-Bu)— | 64 | 709 | 0.29, I (9:1) | 110 |
| 9 | Boc—Arg(Tos)— | -β-Ala— | 50 | 633 | 0.31, I (9:1) | 102 |
| 10 | Boc—Arg(Tos)— | —Ile— | 70 | 675 | 0.24, I (9:1) | 113 | with the corresponding protected arginine derivatives in the presence of bis-(2-oxo-3-oxazolidinyl)-phosphoryl chloride:

TABLE 2

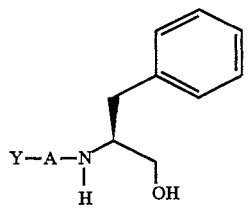

| Ex. No. | Y | A | Yield (% of theory) | MS (FAB) m/z (M + H)⁺ | Rf/eluent ratio | M.p. (°C.) |
|---|---|---|---|---|---|---|
| 12 | Z—Arg(Tos)— | —N—CH₃—Ile | 51 | 723 | 0.13, I (9:1) | foam |
| 13 | Boc—Arg(Tos)— | —N—CH₃—Ala— | 46 | 647 | 0.30, I (9:1) | 102 |
| 14 | Boc—Arg(Tos)— | —N—CH₃—Gly— | 48 | 633 | 0.34, I (9:1) | 102 |
| 15 | Boc—Arg(Tos)— | —Aib— | 36 | 647 | 0.24, I (9:1) | 109 |
| 16 | Z—Arg(Tos)— | —Aib | 48 | 681 | 0.19, I (9:1) | 86 |

The dihydrochlorides described in Table 3 are obtained, in analogy with Example 2, by eliminating the tertbutoxycarbonyl group from the compounds in Tables 1 and 2:

0.64 ml (4.60 mmol) of triethylamine is added to a stirred suspension of 1.30 g (2.00 mmol) of (2S)-2-[N^G-(4-methylphenylsulphonyl)-S-arginyl-S-(tert-butyl)glycinyl]

TABLE 3

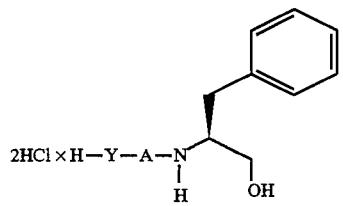

| Ex. No. | Y | —A— | Yield (% of theory) | MS (FAB) m/z (M + H)⁺ | Rf/eluent ratio | M.p. (decomp.) (°C.) |
|---|---|---|---|---|---|---|
| 17 | —Arg(Tos) | —Gly(t-Bu)— | 97 | 575 | 0.34, I (8:2) | 189 |
| 18 | —Arg(Tos)— | —N—CH₃—Ile— | 90 | 589 | 0.01, I (9:1) | 118 |
| 19 | —Arg(Tos)— | —N—CH₃—Ala— | 93 | 547 | 0.12, I (85:15) | 122 |
| 20 | —Arg(Tos)— | —N—CH₃—Gly— | 94 | 533 | 0.08, I (85:15) | 118 |
| 21 | —Arg(Tos)— | -βAla— | 98 | 533 | 0.06, I (85:15) | 130 |
| 22 | —Arg(Tos)— | -Aib- | 95 | 547 | 0.19, I (85:15) | 124 |

Example 23

(2S)-2-{Nα-[3-iso-Propyloxycarbonyl-phenyl)amino-carbonyl]-N^G-(4-methyl-phenylsulphonyl)-S-arginyl-S-(tertbutyl)glycinyl}-amino-3-phenyl-propan-1-ol

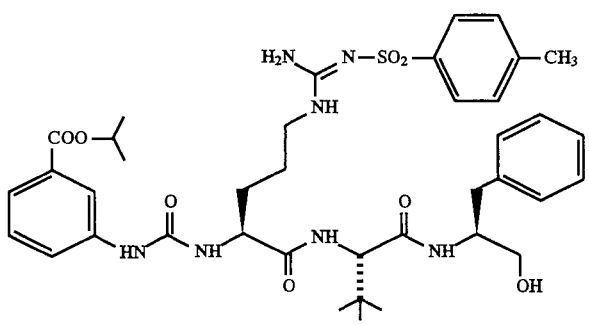

amino-3-phenyl-propan-1-ol dihydrochloride (compound from Example 2) in 40 ml of anhydrous dichloromethane, whereupon a clear solution is obtained. To this are added 490 mg (2.40 mmol) of isopropyl 3-isocyanato-benzoate, and the mixture is subsequently stirred at room temperature for 1 h. 40 ml of toluene are added and the reaction mixture is concentrated in vacuo and the residue purified by chromatography on 170 g of silica gel (dichloromethane:methanol 95:5). The product-containing fractions are collected and concentrated in vacuo. The residue is triturated with 50 ml of ether, separated off by filtration, and dried under high vacuum. 1.01 g (64%) of the title compound are obtained as colourless crystals.

m.p.: 132° C. R_f=0.08 (dichloromethane:methanol 9:1)

MS(FAB): m/z=780 (M+H)⁺, 802 (M+Na)⁺.

The compounds listed in Table 4 are obtained, as described for Example 23, by reacting the compound from Example 2 with the corresponding isocyanates:

TABLE 4

[Structure: compound with H₂N-C(=N-SO₂-C₆H₄-CH₃)-NH-(CH₂)₃- chain attached to backbone of R₇-NH-C(=O)-NH-CH(-)-C(=O)-NH-CH(tBu)-C(=O)-NH-CH(CH₂Ph)-CH₂OH]

| Ex. No. | R⁷ | Yield (% of theory) | MS (FAB) m/z (M + H)⁺ | R$_f$/eluent ratio | M.p. (decomp.) (°C.) |
|---|---|---|---|---|---|
| 24 | pyridin-3-yl-phenyl- (3-pyridyl at one position) | 59 | 771 | 0.23, I (9:1) | 146 |
| 25 | pyridin-4-yl-phenyl- | 53 | 771 | 0.27, I (9:1) | 168 |
| 26 | H₅C₂—OOC—C₆H₄— | 76 | 766 | 0.32, I (9:1) | 136 |
| 27 | n-Bu—OOC—C₆H₄— | 66 | 794 | 0.23, I (9:1) | 141 |
| 28 | CH₃CH₂OCH₂CH₂OOC—C₆H₄— | 75 | 810 | 0.31, I (9:1) | 129 |
| 29 | H₃C—C(=O)—C₆H₄— | 75 | 736 | 0.18, I (9:1) | 142 |

Example 30

(2S)-2-[Nα-Acetyl-N$^G$-(4-methyl-phenylsulphonyl)-S-arginyl-S-(tert-butyl)glycinyl)]-amino-3-phenyl-propan-1-ol

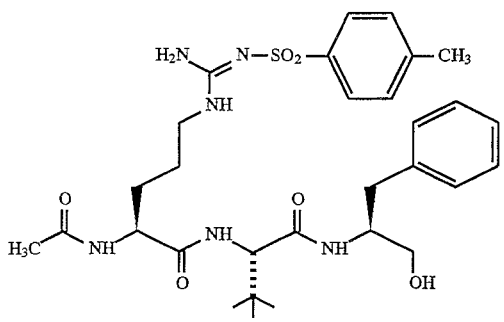

180 μl (1.86 mmol) of acetic anhydride are added dropwise to a solution, which is cooled at 0° C., of 972 mg (1.5 mmol) of the compound from Example 2 in 6 ml of anhydrous dimethyl formamide and 660 μl (6.00 mmol) of N-methylmorpholine. After being kept at 0° C. for 15 min, the mixture is poured into a mixture consisting of 100 ml of ice-cold sodium bicarbonate solution and 50 ml of ethyl acetate, and thoroughly stirred. The organic phase is separated off and the water phase is extracted with 10 ml of ethyl acetate, and the combined organic extracts are dried over magnesium sulphate. After evaporating off the solvent in vacuo, chromatography of the crude product on 45 g of silica gel (dichloromethane:methanol 95:5), and crystallization from 50 ml of dichloromethane:ether 1:10, 394 mg (43%) of the title compound are obtained as colourless crystals.

m.p.: from 114° C. (decomp.) R$_f$=0.24 (dichloromethane:methanol 9:1)

MS(FAB): m/z=617 (M+H)⁺

¹H-NMR (200 MHz, CD₃OD): δ=0.93 (s, 9H, (CH₃)₃—C); 1.4–1.6 (m, 4H, CH₂); 1.95 (s, 3H, CH₃CO); 2.37 (s, 3H, CH₃); 2.68 (dd, J=11, 14 Hz, 1H, CH₂Ph); 2.90 (dd, J=6, 14 Hz, 1H, CH₂Ph); 3.12 (m, 2H, CH₂N); 3.49 (d, J=6 Hz, 2H,

CH₂O); 4.10 (m, 1H, NCH); 4.19 (s, NCHCO); 4.31 (m, 1H, NCH); 7.20 (m, 5H, Ph); 7.29, 7.73 (AB, J=9.5 Hz, 4H, H arom).

Example 31

(2S)-2-[Nα-Quinoline-2-carbonyl-N^G-(4-methyl-phenylsulphonyl)-S-arginyl-S-(tert-butyl)glycinyl]amino-3-phenyl-propan-1-ol

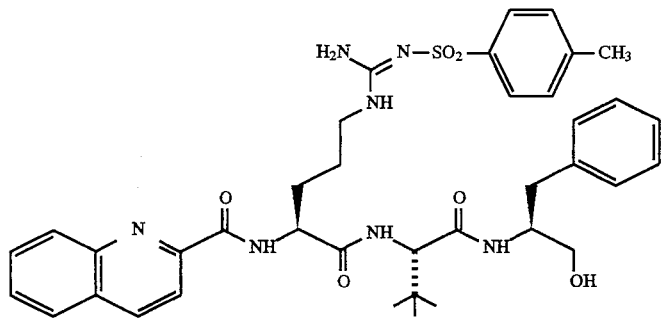

433 mg (2.10 mmol) of DCC are added to a solution, which is cooled at 0° C. and stirred, of 381 mg (2.20 mmol) of quinoline-2-carboxylic acid and 337 mg (2.20 mmol) of HOBT in 30 ml of anhydrous dichloromethane, and the mixture is stirred for 5 min. After that, a solution of 1.29 g (2.00 mmol) of the compound from Example 2 and 0.77 ml (7.00 mmol) of N-methylmorpholine in 30 ml of dichloromethane is added dropwise. The cooling bath is removed and the reaction mixture is left stirring at room temperature for 2 h. The end of the reaction is established by thin layer chromatography. The resulting urea is separated off by filtration and the filtrate is concentrated in vacuo and the crude product purified by chromatography on 80 g of silica gel (dichloromethane:methanol 95:5). 1.14 g (78% of theory) of the title compound are obtained as colourless crystals.

m.p.: 131° C. R_f=0.27 (dichloromethane:methanol 9:1)

MS(FAB): m/z=730 (M+H)⁺

The products listed in Table 5 are obtained, as described for Example 31, by condensing the compound from Example 2:

TABLE 5

| Ex. No. | R⁹ | Yield (% of theory) | MS (FAB) m/z (M + H)⁺ | R_f/eluent ratio | M.p. (decomp.) (°C.) |
|---|---|---|---|---|---|
| 32 | naphthyl-CH₂ | 39 | 743 | 0.27, I (9:1) | 130 |
| 33 | pyridyl-CH₂ | 62 | 680 | 0.32, I (9:1) | 114 |

TABLE 5-continued
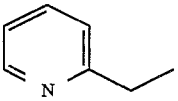
| Ex. No. | R⁹ | Yield (% of theory) | MS (FAB) m/z (M + H)⁺ | R_f/eluent ratio | M.p. (decomp.) (°C.) |
|---|---|---|---|---|---|
| 34 | 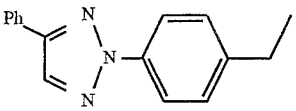 | 44 | 694 | 0.29, I (9:1) | 121 |
| 35 | 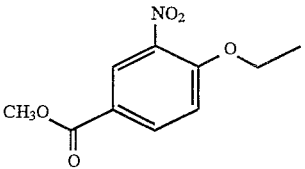 | 71 | 836 | 0.30, I (9:1) | 125 |
| 36 | 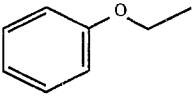 | 72 | 812 | 0.33, I (9:1) | 130 |
| 37 | 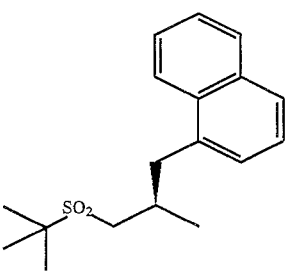 | 68 | 709 | 0.29, I (9:1) | 105 |
| 38 |  | 65 | 891 | 0.36, I (9:1) | 147 |
| 39 | 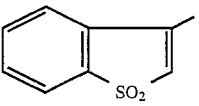 | 65 | 715 | 0.32, I (9:1) | 128 |
| 40 |  | 17 | 767 | 0.28, I (9:1) | 139 |

Example 41

(2S)-2-[Nα-(2,6-Dichloro-phenyl-methoxycarbonyl)-N^G-(4-methyl-phenylsulphonyl)-S-arginyl-S-(tert-butyl)glycinyl]amino-3-phenyl-propan-1-ol

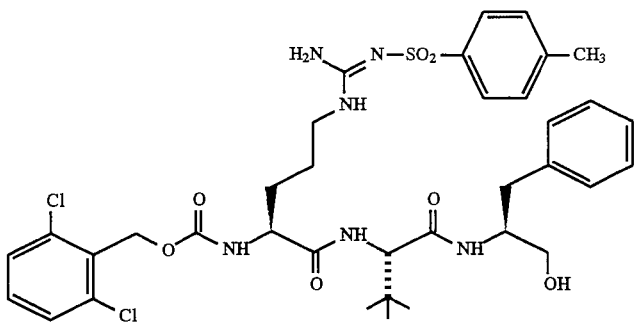

551 mg (2.30 mmol) of 2,6-dichloro-benzyloxycarbonyl chloride are added in portions, within the space of 2 h, to a solution, which is cooled at 0° C. and stirred, of 1.30 g (2.00 mmol) of the compound from Example 2 in 9 ml of dioxane and 6 ml of water, with the pH being maintained at 9–10 by the simultaneous addition of a 2N aqueous solution of NaOH. After that, the mixture is stirred into a mixture of 15 ml of ice water, 6 ml of 1 N citric acid and 30 ml of ethyl acetate. The organic phase is separated off and the water phase is extracted 5 times with 20 ml of ethyl acetate on each occasion. The combined organic extracts are dried over MgSO$_4$. After evaporating off the solvent in vacuo, chromatography of the residue on 75 g of silica gel (dichloromethane:methanol 95:5), and crystallization of the product from 50 ml of ether, 960 mg (61%) of the title compound are obtained as colourless crystals.

m.p.: from 121° C. (decomp.) R$_f$=0.43 (dichloromethane:methanol 9:1) MS(FAB): m/z=777 (M+H)$^+$ $^1$H-NMR (200 MHz, CD$_3$OD) δ=0.96 (s, 9H, [CH$_3$]$_3$C); 1.4–1.6 (m, 4H, CH$_2$); 2.37 (s, 3H, CH$_3$); 2.69 (dd, J=9, 13 Hz, 2H, CH$_2$Ph); 2.90 (dd, J=6, 13 Hz, 2H, CH$_2$Ph); 3.12 (m, 2h, CH$_2$N); 3.50 (d, J=5 Hz, 2H, CH$_2$O); 4.10 (m, 2H, NCH); 4.20 (s, 1H, NCHCO); 5.36 (s, 2H, CH$_2$OCO); 7.15–7.45 (m, 8H, H arom.); 7.28, 7.72 (AB, J=8.5 Hz, 4H, H arom).

The compounds listed in Table 6 are obtained, as described for Example 41, by reacting the compound from Example 2 with the corresponding benzyloxycarbonyl chlorides:

TABLE 6

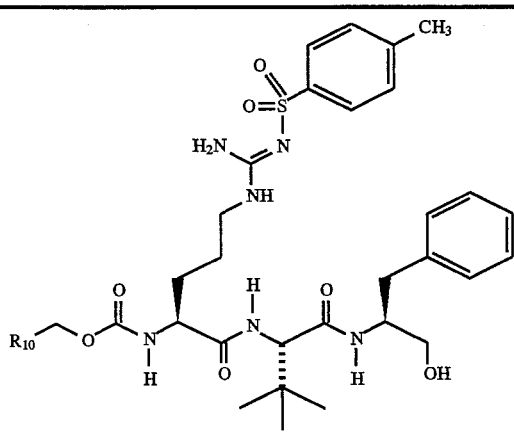

| Ex. No. | R$^{10}$ | Yield (% of theory) | MS (FAB) m/z (M + H)$^+$ | R$_f$/eluent ratio | M.p. (decomp.) (°C.) |
|---|---|---|---|---|---|
| 42 | C$_6$H$_5$— | 64 | 709 | 0.29, I (9:1) | 110 |
| 43 | 4-NO$_2$—C$_6$H$_4$— | 68 | 754 | 0.39, I (9:1) | 115 |
| 44 | 2,5-CH$_3$—C$_6$H$_3$— | 42 | 737 | 0.21, I (9:1) | 105 |

Example 45

(2S)-2-[Nα-(3-Pyridinyl-methoxycarbonyl)-N^G-(4-methylphenylsulphonyl)-S-arginyl-S-(tert-butyl) glycinyl]amino-3-phenyl-propan-1-ol

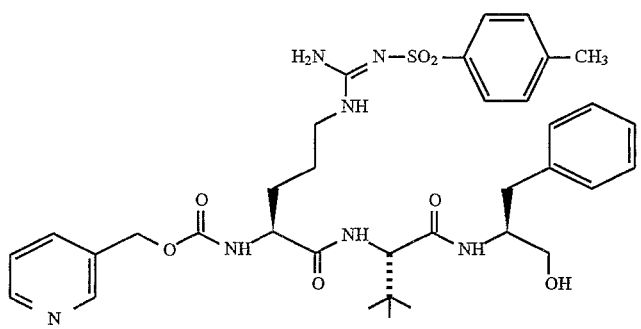

A stirred suspension of 1.30 g (2.00 mmol) of the compound from Example 2 and 1.10 g (4.00 mmol) of 4-nitrophenyl-3-pyridinylmethyl carbonate [prepared in accordance with D. F. Veber et al., J. Org. Chem. 42, 3286 (1977)] in 10 ml of dioxane and 10 ml of water is maintained at pH 7.5 by continually adding an aqueous 2N solution of NaOH (requirement about 2.5 ml), and stirred at room temperature for 15 h. The end of the reaction is established by thin layer chromatography, and the reaction mixture is then stirred into a mixture consisting of 25 ml of 1N citric acid and 20 ml of ethyl acetate. The aqueous phase is separated off, adjusted to pH 9 by adding 2N NaOH, and then extracted with 20 ml of ethyl acetate (3 times). The combined organic extracts are dried over MgSO$_4$. The solvent is evaporated off in vacuo and the residue is crystallized from dichloromethane/ether. 1.15 g (81%) of the title compound are obtained as colourless crystals.

m.p.: from 88° C. (decomp.) R$_f$=0.12 (dichloromethane:methanol 9:1)

MS(FAB): m/z=710 (M+H)$^+$ $^1$H-NMR (200 MHz, CD$_3$OD) δ=0.92 (s, 9H, [CH$_3$]$_3$C); 1.4–1.6 (m, 4H, CH$_2$); 2.37 (s, 3H, CH$_3$); 2.68 (dd, J=8, 14 Hz, 1H, CH$_2$Ph); 2.90 (dd, J=6, 14 Hz, 1H, CH$_2$Ph); 3.12 (m, 2H, CH$_2$N); 3.50 (m, 2H, CH$_2$O); 4.10 (m, 2H, CH); 4.18 (s, 1H, NCHCO); 5.15 (s, 2H, CH$_2$OCO); 7.18 (m, 5H, Ph); 7.27, 7.72 (AB, J=8 Hz, 4H, H arom.); 7.41 (dd, J=5, 7 Hz, 1H, 5-Pyridyl-H); 7.85 (m, 1H, 4-Pyridyl-H); 8.45 (dd, J=1.5 Hz, 6-Pyridyl-H); 8.55 (d, J=1 Hz, 1H, 2-Pyridyl-H ).

The compounds listed in Table 7 are obtained, as described for Example 45, by reacting the compound from Example 2 with the corresponding 4-nitrophenyl carbonates:

TABLE 7

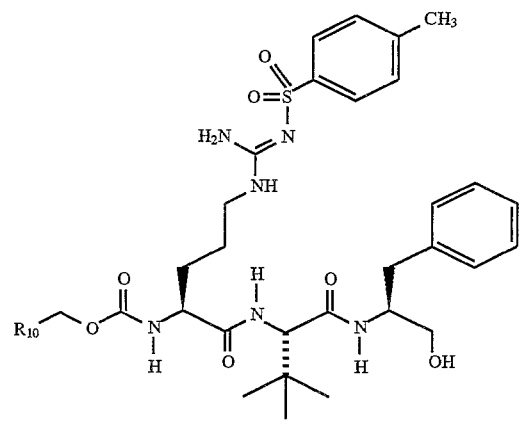

| Ex. No. | R$^{10}$ | Yield (% of theory) | MS (FAB) m/z (M + H)$^+$ | R$_f$/eluent ratio | M.p. (decomp.) (°C.) |
|---|---|---|---|---|---|
| 46 | (2-pyridyl) | 2 | 710 | 0.27, I (9:1) | 98 |
| 47 | (4-pyridyl) | 25 | 710 | 0.28, I (9:1) | 120 |

TABLE 7-continued

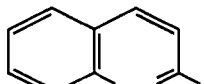

| Ex. No. | R¹⁰ | Yield (% of theory) | MS (FAB) m/z (M + H)⁺ | R_f/eluent ratio | M.p. (decomp.) (°C.) |
|---|---|---|---|---|---|
| 48 | (quinolin-2-yl) | 11 | 760 | 0.35, I (9:1) | amorphous |
| 49 | (6-methylpyridin-2-yl) | 17 | 724 | 0.30, I (9:1) | foam |

Example 50

(2R,S)-2-[Nα-(Benzyloxycarbonyl)-N^G-(4-methyl-phenylsulphonyl)-S-arginyl-S-(tert-butyl)glycinyl]amino-3-phenyl-propan-1-al

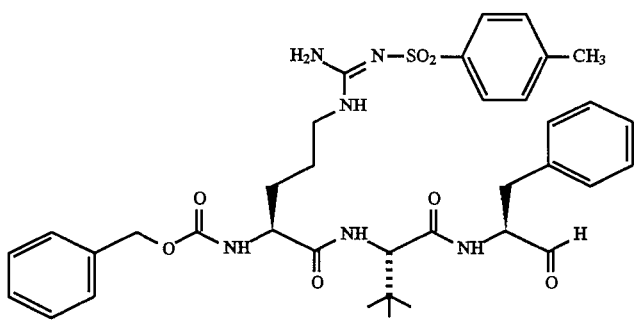

221 mg (1.39 mmol) of pyridine sulphur trioxide complex are added to a solution of 218 mg (0.31 mmol) of the compound from Example 8 in 2.5 ml of anhydrous DMSO and 0.39 ml (2.77 mmol) of triethylamine, and the mixture is stirred at room temperature for 1 h. After that, the reaction mixture is stirred into 20 ml of ether. The mixture is left to stand for a short period, during which an oil separates out. The ether phase is decanted off and the oil is taken up in 5 ml of toluene. The toluene is evaporated off in vacuo and the residue is chromatographed on 43 g of silica gel (dichloromethane:methanol 95:5). 195 mg (89%) of the title compound are obtained as a pale yellow oil (diastereomeric mixture).

R_f=0.25, 0.33 (dichloromethane:methanol 9:1) MS(FAB): m/z=707 (M+H)⁺

The compounds listed in Tables 8 and 9 are obtained as mixtures of the diastereomeric aldehydes, as described for Example 50, by oxidizing the alcohols from the previous tables:

TABLE 8

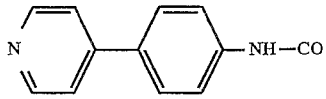

| Ex. No. | Y— | A | Yield (% of theory) | MS (FAB) m/z (M + H)+ | R$_f$/eluent ratio | M.p. (decomp.) (°C.) |
|---|---|---|---|---|---|---|
| 51 | Boc—Arg(Tos)— | — | 57 | 560 | 0.69, I (85:15)99 | |
| 52 | Boc—Arg(Tos)— | Gly(t-Bu)— | 76 | 673 | 0.22, 0.27, II (9:1) | Oil |
| 53 | Z—Arg(Tos)— | Gly(t-Bu)— | 96 | 707 | 0.39, 0.44, I (9:1) | Foam |
| 54 | Boc—Arg(Tos)— | N—CH$_3$—Ile— | 56 | 687 | 0.14, I (9:1) | Foam |
| 55 | Z—Arg(Tos)— | N—CH$_3$—Ile— | 47 | 721 | 0.20, I (9:1) | Foam |
| 56 | Boc—Arg(Tos)— | Ile | 55 | 673 | 0.41, 0.44, I (9:1) | Foam |
| 57 | Boc—Arg(Tos)— | N—CH$_3$—Ala— | 72 | 645 | 0.41, 0.45, I (9:1) | Foam |
| 58 | Boc—Arg(Tos)— | N—CH$_3$—Gly— | 89 | 631 | 0.40, I (9:1) | Foam |
| 59 | Boc—Arg(Tos)— | β—Ala— | 66 | 631 | 0.30, I (9:1) | Foam |
| 60 | Boc—Arg(Tos)— | Aib— | 90 | 645 | 0.13, I (9:1) | Oil |
| 61 | Z—Arg(Tos)— | Aib— | 60 | 679 | 0.53, I (9:1) | Foam |

TABLE 9

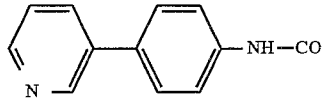

| Ex. No. | R$^1$ | Yield (% of theory) | MS (FAB) m/z (M + H)+ | R$_f$/eluent ratio | M.p. (decomp.) (°C.) |
|---|---|---|---|---|---|
| 62 | 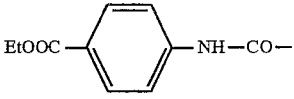 | 22 | 769 | 0.17, 0.21, I (9:1) | 151 (decomp.) |
| 63 | 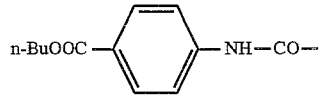 | 37 | 769 | 0.22, 0.31, (9:1) | 100 (decomp.) |
| 64 | EtOOC—⟨phenyl⟩—NH—CO— | 54 | 764 | 0.29, 0.33 (9:1) | 121 |
| 65 | n-BuOOC—⟨phenyl⟩—NH—CO— | 55 | 792 | 0.29, 0.33 (9:1) | 120 |

TABLE 9-continued

| Ex. No. | R¹ | Yield (% of theory) | MS (FAB) m/z (M + H)⁺ | R_f/eluent ratio | M.p. (decomp.) (°C.) |
|---|---|---|---|---|---|
| 66 | CH₃—CH₂—O—CH₂CH₂OOC—⟨C₆H₄⟩—NH—CO— | 63 | 808 | 0.24, 0.28, (9:1) | 112 |
| 67 | H₃C-CO—⟨C₆H₄⟩—NH—CO— | 62 | 734 | 0.37, 0.42 (9:1) | 137 |
| 68 | H₃C-CO— | 54 | 615 | 0.23, I (9:1) | 122 (decomp.) |
| 69 | quinolin-2-yl-CO— | 88 | 728 | 0.43, 0.49, I (9:1) | foam 131 (decomp.)³⁾ |
| 70 | pyridin-2-yl-CO— | 87 | 678 | 0.36, 0.39, I (19:1) | foam |
| 71 | pyridin-2-yl-CH₂-CO— | 59 | 692 | 0.30, 0.40, I (9:1) | 115 (decomp.) |
| 72 | naphth-2-yl-CH₂-CO— | 79 | 741 | 0.39, 0.41, I (9:1) | Oil |
| 73 | 2,6-dichlorobenzyl-O-CO-CH₂— | 96 | 775 | 0.26, 0.31, I (9:1) | foam |
| 74 | 4-nitrobenzyl-O-CO-CH₂— | 87 | 752 | 0.41, 0.46, I (9:1) | foam |

TABLE 9-continued
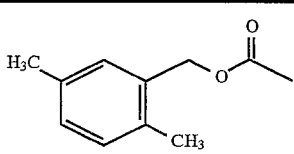
| Ex. No. | R¹ | Yield (% of theory) | MS (FAB) m/z (M + H)⁺ | R$_f$/eluent ratio | M.p. (decomp.) (°C.) |
|---|---|---|---|---|---|
| 75 | 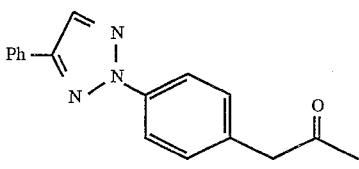 | 36 | 735 | 0.35, 0.39, I (19:1) | foam |
| 76 | 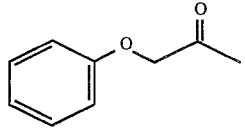 | 81 | 940[2)] | 0.36, 0.39, I (9:1) | foam |
| 77 | 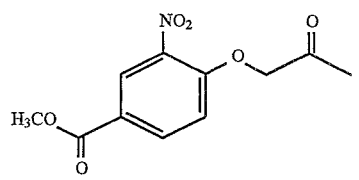 | 96 | 707 | 0.39, 0.44, I (9:1) | foam |
| 78 | 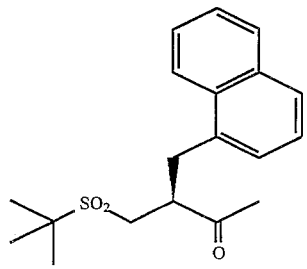 | 37 | 810 | 0.45, 0.50, I (9:1) | 105 (decomp.) |
| 79 | 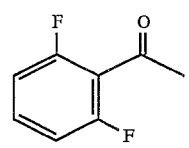 | 48 | 889 | 0.46, I (9:1) | 128 (decomp.) |
| 80 |  | 96 | 713 | 0.53, 0.57, I (19:1) | foam |

TABLE 9-continued

| Ex. No. | R¹ | Yield (% of theory) | MS (FAB) m/z (M + H)⁺ | $R_f$/eluent ratio | M.p. (decomp.) (°C.) |
|---|---|---|---|---|---|
| 81 | (3-acetyl-benzothiophene-SO₂) | 49 | 765 | 0.39, 0.42, (9:1) | oil |
| 82 | (pyridin-3-yl-methyl acetate · 2 HCl) | 44 | 708 | 0.23, 0.26, I (9:1) | 112 (decomp.)[3] |
| 83 | (pyridin-4-yl-methyl acetate · 2 HCl) | 30 | 708 | 0.24, 0.28, I (9:1) | 98 (decomp.)[3] |
| 84 | (6-methyl-pyridin-2-yl-methyl acetate) | 37 | 722 | 0.26, 0.30, I (9:1) | foam |
| 85 | (quinolin-2-yl-methyl acetate) | 51 | 758 | 0.33, 0.36, I (9:1) | amorphous |

[3] = Hydrochloride

Example 86

(2R.S)-2-{Nα-[(4-(3-Pyridinyl)-phenyl)
aminocarbonyl]-N^G-(4-methylphenyl-sulphonyl)-S-
arginyl-S-(tert-butyl)glycinyl}-amino-3-phenyl-
propan-1-al dihydrochloride

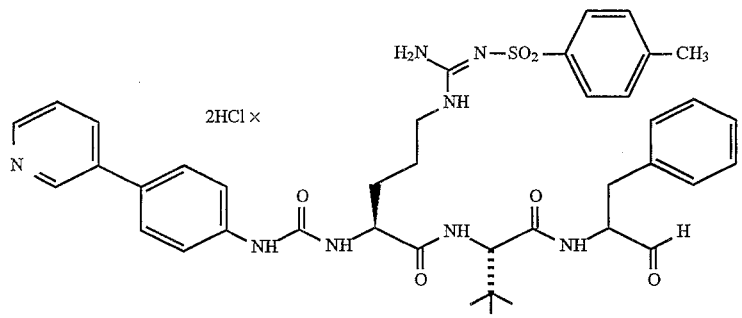

4 ml of a 1N solution of gaseous hydrogen chloride in ether are added dropwise to a stirred solution of 226 mg (0.29 mmol) of the compound from Example 63 in 4 ml of anhydrous dioxane. The mixture is stirred at room temperature for 30 min and 20 ml of ether are added; the precipitate is then separated off by filtration and drying takes place under high vacuum. 205 mg (81%) of the title compound are obtained as colourless crystals (mixture of the diastereomeric aldehydes).

m.p.: from 98° C. (decomp.) $R_f$=0.22, 0.33 (dichloromethane:methanol 9:1) MS(FAB): m/z=769 (M+H)$^+$ The examples in Table 10 are prepared in analogy with the instructions in Example 45 and the comments on the compounds listed in Table 7:

TABLE 10

| Ex. No. | R$^{10}$ | Yield (% of theory) | MS (FAB) m/z (M + H)$^+$ | R$_f$/eluent ratio | M.p. (decomp.) (°C.) |
|---|---|---|---|---|---|
| 87 | 2-ethyl-pyridinyl | 22 | 724 | 0.23, I (9:1) | 106 |
| 88 | 3-(1-methyl)-pyridinyl | 30 | 724 | 0.27, I (9:1) | 124 (decomp.) |

TABLE 10-continued

[Structure: tosyl-guanidino arginine derivative with R10-O-CO-NH backbone, tert-butyl group, phenyl, and terminal -OH]

| Ex. No. | R¹⁰ | Yield (% of theory) | MS (FAB) m/z (M + H)⁺ | R_f/eluent ratio | M.p. (decomp.) (°C.) |
|---|---|---|---|---|---|
| 89 | 3-pyridyl-propyl | 45 | 738 | 0.32, I (9:1) | 100 (decomp.) |
| 90 | 2-pyridyl-propyl | 31 | 738 | 0.30, I (9:1) | 116 (decomp.) |
| 91 | 6-methyl-2-pyridyl-propyl | 46 | 752 | 0.29, I (9:1) | 86 (decomp.) |

The examples in Table 11 are prepared in analogy with the instructions in Example 50 and the comments on the compounds in Tables 8 and 9:

TABLE 11

[Structure: tosyl-guanidino arginine derivative with R¹-NH backbone, tert-butyl group, phenyl, and terminal aldehyde -CHO]

| Ex. No. | R¹ | Yield (% of theory) | MS (FAB) m/z (M + H)⁺ | R_f/eluent ratio | M.p. (decomp.) (°C.) |
|---|---|---|---|---|---|
| 92 | 2 × HCl, 2-pyridyl-CH₂CH₂-O-CO- | 66 | 722 | 0.25/0.27, I (9:1) | 145 (decomp.)[3] |

TABLE 11-continued

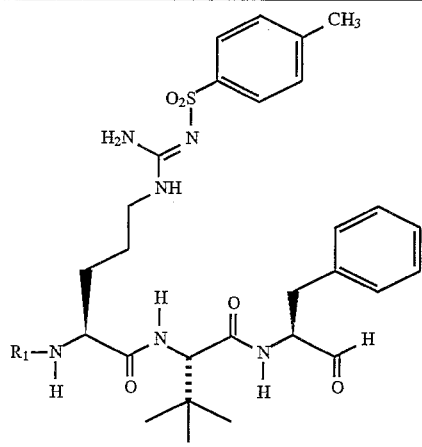

| Ex. No. | R¹ | Yield (% of theory) | MS (FAB) m/z (M + H)⁺ | $R_f$/eluent ratio | M.p. (decomp.) (°C.) |
|---|---|---|---|---|---|
| 93 | ![structure] | 65 | 722 | 0.26/0.29, I (9:1) | 108 (decomp.) |
| 94 | ![structure] | 33 | 736 | 0.30/0.33, I (9:1) | amorphous |
| 95 | 2 × HCl ![structure] | 17 | 736 | 0.22/0.25, I (9:1) | Lyophilisate |
| 96 | 2 × HCl ![structure] | 28 | 750 | 0.41/0.43, I (9:1) | Lyophilisate |

3) ≦ Hydrochloride

We claim:

1. A pseudopepetide of the formula

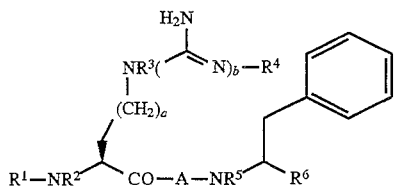

in which
a represents a number 1, 2 or 3,
b represents a number 0 or 1,
R¹ represents hydrogen, or represents an amino protecting group selected from the group consisting of allyloxycarbonyl, vinyloxycarbonyl, cyclohexyloxycarbonyl, adamantylcarbonyl, phthaloyl, 2,2,2-trichloroethoxycarbonyl, 2,2,2-trichloro-tert-butoxycarbonyl, menthyloxycarbonyl, fluorenyl-9-methoxycarbonyl, formyl, acetyl, propionyl, pivaloyl, 2-chloroacetyl, 2-bromoacetyl, 2,2,-trifluoroacetyl, phthalimido, isovaleroyl, or represents a radical of the formula R⁷—NR⁸—CO—, R⁹—(CH₂)_c—CO—, R¹⁰—(CH₂)_d—O—CO, or represents a radical of the formula —SO₂—R¹¹, in which R⁷ denotes cycloalkyl having 3 to 6 carbon atoms, or denotes straight-chain or branched alkyl having up to 18 carbon atoms which is optionally substituted by hydroxyl, straight-chain or branched alkoxy having up to 4 carbon atoms, halogen, trifluoromethyl, trifluoromethoxy or cycloalkyl having 3 to 6 carbon atoms, or substituted by aryl having 6 to 10 carbon atoms which in turn is substituted identically or optionally differently up to 2 times by carboxyl, cyano, hydroxyl, halogen, perhalogenoalkyl having up to 5 carbon atoms, or by straight-chain of branched acyl, having up 6 carbon atom, alkoxy, having up to 6 carbon atoms or alkoxy carbonyl having up to 6 carbon atoms, or alkyl is optionally substituted by a group of the formula —$CO_2R^{12}$, in which $R^{12}$ denotes hydrogen, or straight-chain or branched alkyl or alkenyl having in each case up to 8 carbon atoms which are optionally substituted by phenyl, or $R^7$ denotes aryl having 6 to 10 carbon atoms which is optionally substituted identically or differently up to 3 times by carboxyl, amino, halogen, hydroxyl, cyano, perhalogenoalkyl having up to 5 carbon atoms, or substituted by straight-chain or branched acyl, alkoxy, vinyl alkoxy, carbonyl, alkoxycarbonyl or having in each case up to 6 carbon atoms, which in turn is substituted by straight-chain or branched alkoxy having up to 6 carbon atoms, or denotes an amino acid radical of the formula

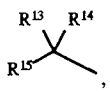

in which $R^{13}$ and $R^{14}$ are identical or different and denote hydrogen or methyl, or $R^{13}$ and $R^{14}$ together form a 5- or 6-membered saturated carbocyclic ring, or $R^{13}$ denotes hydrogen or methyl, and $R^{14}$ denotes cycloalkyl having 3 to 8 carbon atoms or aryl having 6 to 10 carbon atoms, or hydrogen, or straight-chain or branched alkyl having up to 8 carbon atoms where the alkyl is optionally substituted by methylthio, hydroxyl, mercapto or guanidyl, or by a group of the formula —$NR^{16}R^{17}$ or $R^{18}$—OC—, in which $R^{16}$ and $R^{17}$, independently of each other, denote hydrogen, straight-chain or branched alkyl having up to 8 carbon atoms, or phenyl, and $R^{18}$ denotes hydroxyl, benzyloxy, alkoxy having up to 6 carbon atoms, or the above listed group —$NR^{16}R^{17}$, $R^{15}$ denotes straight-chain or branched alkyl having up to 8 carbon atoms which is optionally substituted by hydroxyl or straight-chain or branched alkoxy having up to 6 carbon atoms, or denotes carboxyl, allyloxycarbonyl, straight-chain or branched alkoxycarbonyl having up to 8 carbon atoms, or benzyloxycarbonyl, or the alkyl is optionally substituted by cycloalkyl having 3 to 8 carbon atoms, or substituted by aryl having 6 to 10 carbon atoms which, for its part, is optionally substituted by hydroxyl, halogen, nitro, alkoxy having up to 8 carbon atoms, or substituted by the group —$NR^{16}R^{17}$, in which $R^{16}$ and $R^{17}$ have the abovementioned meaning, or the alkyl is optionally substituted by a 5- to 6-membered nitrogen-containing heterocycle in which the —NH— functions are optionally substituted by alkyl having up to 6 carbon atoms or by an amino protective group, $R^7$ denotes a radical of the formula,

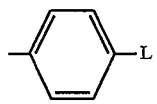

in which

L denotes phenyl or pyridyl, $R^8$ denotes hydrogen, straight-chain or branched alkyl having up to 6 carbon atoms, or an amino-protective group, $R^9$ denotes straight-chain or branched alkyl having up to 8 carbon atoms, which is optionally substituted by pyridyl or phenyl, or aryloxy or aryl having in each case 6 to 10 carbon atoms, indolyl, quinolyl, quinoxalilyl, isoquinolyl, or a 5- to 7-membered, saturated or unsaturated, heterocycle having up to 3 heteroatoms selected from the group consisting of S, N or O, wherein said rings are substituted identically or differently up to 3 times by carboxyl, cyano, hydroxyl, halogen, amino, nitro, methylamino, perhalogenoalkyl having up to 5 carbon atoms, or substituted by straight-chain or substituted by straight-chain or branched alkyl, acyl, alkoxy or alkoxycarbonyl having in each base up to 6 carbon atoms, or aryl is also optionally substituted by a 5- to 7-membered, saturated or unsaturated, heterocycle having up to 3 heteroatoms selected from the group consisting of S, N or O, which in turn is optionally substituted by phenyl, or $R^9$ denotes a radical of the formula

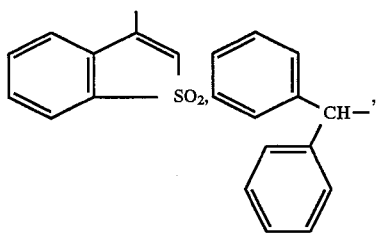

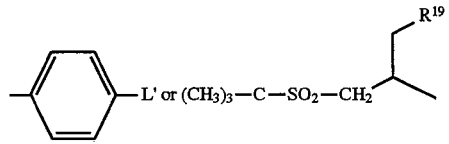

in which

L' has the abovementioned meaning of L and is identical to or different from the latter, $R^{19}$ denotes phenyl or naphthyl, c denotes a number 0, 1, 2 or 3, d denotes a number 0, 1, 2 or 3, $R^{10}$ has the abovementioned meaning of $R^9$ and is identical to or different from the latter, $R^{11}$ denotes methyl, phenyl or naphthyl which is optionally substituted identically or differently up to 4 times by methyl or methoxy, or denotes a radical of the formula

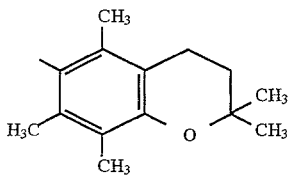

$R^2$, $R^3$ and $R^5$ are identical or different and represent hydrogen or straight-chain or branched alkyl having up to 4 carbon atoms, or represent an aminoprotective group, $R^4$ represents an aminoprotective group or a group of the formula $SO_2$—$R^{20}$ in which $R^{20}$ independently has any of the above mentioned meanings of $R^{11}$ A represents a bond or a radical of the formula

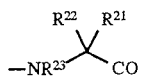

in which $R^{21}$ and $R^{22}$ are identical or different and have the abovementioned meaning of $R^{13}$ and $R^{14}$ and are identical to or different from the latter, $R^{23}$ independently has any of the abovementioned meanings of $R^2$, $R^3$ or $R^5$, $R^6$ represents formyl or carboxyl, or represents straight-chain or branched alkoxycarbonyl having up to 8 carbon atoms, or represents a radical of the formula —$CH_2$—$OR^{24}$ or —$CH(OR^{25})_2$, in which $R^{24}$ and $R^{25}$ are identical or different and denote hydrogen, straight-chain or branched alkyl having up to 6 carbon atoms, or a hydroxyl protective group, or a pharmaceutically acceptable salt thereof, with the proviso that A must not represent valine.

2. A compound or salt thereof according to claim 1, in which a represents a number 2 or 3, b represents a number 0 or 1, $R^1$ represents hydrogen, 9-fluorenylmethoxycarbonyl or represents a radical of the formula $R^7$—$NR^8$—CO—, $R^9$—$(CH_2)_c$—CO—, $R^{10}$—$(CH_2)_d$—O—CO, or a radical of the formula —$SO_2$—$R^{11}$, in which $R^7$ denotes cyclopentyl or cyclohexyl, or straight-chain or branched alkyl having up to 16 carbon atoms which is optionally substituted by hydroxyl, methoxy, fluorine, chlorine, bromine, trifluoromethyl, trifluoromethoxy, cyclopentyl or cyclohexyl, or phenyl which in turn is optionally substituted identically or differently up to 2 times by carboxyl, cyano, hydroxyl, fluorine, chlorine, bromine or perhalogenoalkyl having up to 4 carbon atoms, or by straight-chain or branched acyl, alkoxy or alkoxycarbonyl having in each case up to 4 carbon atoms, or alkyl is optionally substituted by a group of the formula —$CO_2R^{12}$, in which $R^{12}$ denotes hydrogen, or straight-chain or branched alkyl or alkenyl having in each case up to 6 carbon atoms which are optionally substituted by phenyl, or $R^7$ denotes phenyl, or naphthyl which is optionally substituted identically or differently up to 3 times by carboxyl, amino, fluorine, chlorine, bromine, hydroxyl, cyano or perhalogenoalkyl having up to 4 carbon atoms, or by straight-chain or branched acyl, alkoxy, vinylalkoxycarbonyl or alkoxycarbonyl having in each case up to 5 carbon atoms which in turn is substituted by straight-chain or branched alkoxy having up to 6 carbon atoms, or denotes an amino acid radical of the formula $$R^{15} \diagup\!\!\!\diagdown \begin{matrix} R^{13} & R^{14} \end{matrix},$$

in which $R^{13}$ and $R^{14}$ are identical or different and denote hydrogen or methyl, or $R^{13}$ and $R^{14}$ together form a cyclopentyl or cyclohexyl ring, or $R^{13}$ denotes hydrogen or methyl, and $R^{14}$ denotes cyclopropyl, cyclopentyl, cyclohexyl, phenyl or hydrogen, or denotes straight-chain or branched alkyl having up to 6 carbon atoms, where the alkyl is optionally substituted by methylthio, hydroxyl, mercapto or guanidyl, or by a group of the formula —$NR^{16}R^{17}$ or $R^{18}$—OC—, in which $R^{16}$ and $R^{17}$, independently of each other, denote hydrogen, straight-chain or branched alkyl having up to 6 carbon atoms, or phenyl, and $R^{18}$ denotes hydroxyl, benzyloxy, alkoxy having up to 6 carbon atoms, or the above-listed group —$NR^{16}R^{17}$, or the alkyl is optionally substituted by cyclopropyl, cyclopentyl or cyclohexyl, or by phenyl which is substituted by hydroxyl, fluorine, chlorine, bromine, nitro or alkoxy having up to 8 carbon atoms, or by the group $NR^{16}R^{17}$, in which $R^{16}$ and $R^{17}$ have the abovementioned meaning, or the alkyl is optionally substituted by imidazolyl or indolyl in which the corresponding —NH— functions are optionally protected by alkyl having up to 6 carbon atoms or by an aminoprotective group, $R^{15}$ denotes straight-chain or branched alkyl having up to 6 carbon atoms which is optionally substituted by hydroxyl or by straight-chain or branched alkoxy having up to 4 carbon atoms, or denotes carboxyl, allyloxycarbonyl, straight-chain or branched alkoxycarbonyl having up to 6 carbon atoms, or benzyloxycarbonyl, $R^7$ denotes a radical of the formula —⟨phenyl⟩—L in which L denotes phenyl or pyridyl, $R^8$ denotes hydrogen, straight-chain or branched alkyl having up to 4 carbon atoms, tert-butoxycarbonyl (Boc) or benzyloxycarbonyl (Z), $R^9$ denotes straight-chain or branched alkyl having up to 6 carbon atoms, which is optionally substituted by phenyl, or denotes phenoxy, phenyl, napthyl, indolyl, quinolyl, quinoxalinyl, isoquinolyl, pyridyl, pyrazinyl pyrimidyl, triazolyl or imidazolyl, wherein said rings are optionally substituted identically or differently up to 3 times by nitro, carboxyl, cyano, hydroxyl, fluorine, chlorine, bromine, perhalogenoalkyl having up to 4 carbon atoms, or by straight-chain or branched alkyl, acyl, alkoxy or alkoxycarbonyl having in each case up to 4 carbon atoms, or phenyl is optionally substituted by pyridyl or triazolyl, where the latter two can in turn be substituted by phenyl, or $R^9$ denotes a radical of the formula

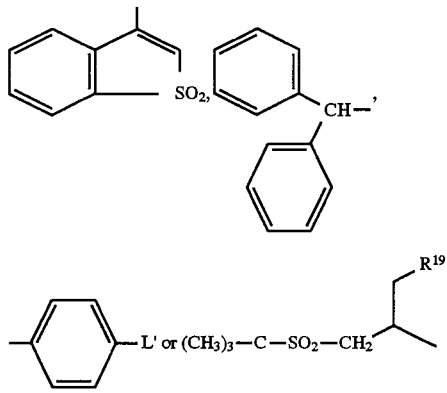

in which

L' has the abovementioned meaning of L and is identical to or different from the latter, $R^{19}$ denotes phenyl or naphthyl, c denotes a number 0, 1, 2 or 3, d denotes a number 0, 1 or 2, $R^{10}$ has the abovementioned meaning of $R^9$ and is identical to or different from the latter, $R^{11}$ denotes methyl, or phenyl which is optionally substituted identically or differently up to 4 times by methyl or methoxy, or denotes a radical of the formula

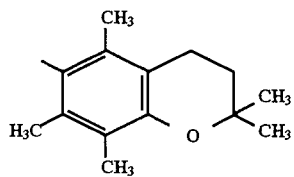

$R^2$, $R^3$ and $R^5$ are identical or different and denote Boc, hydrogen, methyl, ethyl, benzyloxycarbonyl or tert-butyl, $R^4$ represents benzyloxycarbonyl, tert-butoxycarbonyl or a radical of the formula —$SO_2R^{20}$, in which $R^{20}$ independently has any of the abovementioned meanings of $R^{11}$, A represents a bond or a radical of the formula

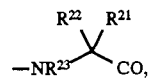

in which $R^{21}$ and $R^{22}$ are identical or different and have the abovementioned meaning of $R^{13}$ and $R^{14}$ and are identical to or different from the latter, $R^{23}$ has the abovementioned meaning of $R^2$, $R^3$ or $R^5$ and is identical to or different from the latter, $R^6$ represents formyl or carboxyl, or represents straight-chain or branched alkoxycarbonyl having up to 6 carbon atoms, or represents a radical of the formula —$CH_2$—$OR^{24}$ or —$CH(OR^{25})_2$, in which $R^{24}$ and $R^{25}$ are identical or different and denote hydrogen, straight-chain or branched alkyl having up to 4 carbon atoms, acetyl or benzyl.

3. A compound or salt thereof according to claim 1, in which a represents a number 2 or 3, b represents a number 0 or 1, $R^1$ represents hydrogen or represents a radical of the formula $R^7$—$NR^8$—CO—, $R^9$—$(CH_2)_c$—CO—, $R^{10}$—$(CH_2)_dO$—CO, or represents a radical of the formula —$SO_2$—$R^{11}$, in which $R^7$ denotes cyclopentyl or cyclohexyl, or straight-chain or branched alkyl having up to 14 carbon atoms which is optionally substituted by hydroxyl, methoxy, fluorine, trifluoromethyl, trifluoromethoxy or cyclohexyl, or phenyl which is optionally substituted by a group of the formula —$CO_2R^{12}$, in which $R^{12}$ denotes hydrogen, or straight-chain or branched alkyl or alkenyl having in each case up to 4 carbon atoms, or benzyl, or $R^7$ denotes phenyl which is optionally substituted identically or differently up to 3 times by carboxyl, fluorine, hydroxyl, cyano, trifluoromethyl or amino, or by straight-chain or branched acyl, alkoxy, vinylalkoxycarbonyl or alkoxycarbonyl having in each case up to 4 carbon atoms, which in turn is substituted by straight-chain or branched alkoxy having up to 4 carbon atoms, or denotes an amino acid radical of the formula

in which $R^{13}$ and $R^{14}$ are identical or different and denote hydrogen or methyl, or $R^{13}$ and $R^{14}$ together form a cyclopentyl or cyclohexyl ring, or $R^{13}$ denotes hydrogen or methyl, and $R^{14}$ denotes cyclopropyl, cyclopentyl, cyclohexyl, phenyl or hydrogen, or denotes straight-chain or branched alkyl having up to 6 carbon atoms, where the alkyl is optionally substituted by methylthio, hydroxyl, mercapto or guanidyl, or by a group of the formula —$NR^{16}R^{17}$ or $R^{18}$—OC—, in which $R^{16}$ and $R^{17}$ independently of each other, denote hydrogen, straight-chain or branched alkyl having up to 6 carbon atoms, or phenyl, and $R^{18}$ denotes hydroxyl, benzyloxy, alkoxy having up to 4 carbon atoms, or the above-listed group —$NR^{16}R^{17}$, or the alkyl is optionally substituted by cyclopropyl, cyclopentyl or cyclohexyl, or phenyl which in turn is substituted by hydroxyl, fluorine, chlorine, bromine, nitro, alkoxy having up to 6 carbon atoms, or by the group —$NR^{16}R^{17}$, in which $R^{16}$ and $R^{17}$ have the abovementioned meaning, or the alkyl is optionally substituted by imidazolyl or indolyl in which the corresponding —NH— functions are optionally protected by alkyl having up to 4 carbon atoms, tert-butoxycarbonyl or benzyloxycarbonyl, $R^{15}$ denotes straight-chain or branched alkyl having up to 4 carbon atoms which is optionally substituted by hydroxyl or straight-chain or branched alkoxy having up to 3 carbon atoms, or denotes carboxyl, allyloxcarbonyl, straight-chain or branched alkoxycarbonyl having up to 4 carbon atoms, or benzyloxycarbonyl, or $R^7$ denotes a radical of the formula

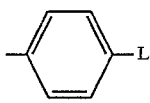

in which

L denotes phenyl or pyridyl, $R^8$ denotes hydrogen, methyl, ethyl or tert-butyl, $R^9$ denotes straight-chain or branched alkyl having up to 6 carbon atoms, which is optionally substituted by pyridyl, phenoxy, phenyl, naphthyl, indolyl, quinolyl, quinoxalinyl, isoquinolyl, pyridyl, pyrazinyl, pyrimidyl, triazolyl or imidazolyl, where the rings are optionally substituted identically or differently up to 3 times by nitro, carboxyl, cyano, hydroxyl, fluorine, chlorine, bromine, perhalogenoalkyl having up to 4 carbon atoms, or by straight-chain or branched alkyl, acyl, alkoxy or alkoxycarbonyl having in each case up to 4 carbon atoms, or phenyl is optionally substituted by pyridyl or triazolyl, where the latter can, in turn, he substituted by phenyl, or $R^9$ denotes a radical of the formula

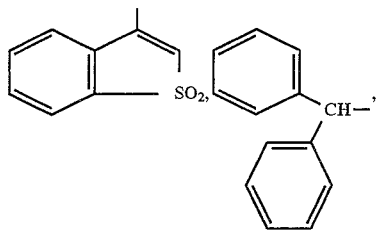

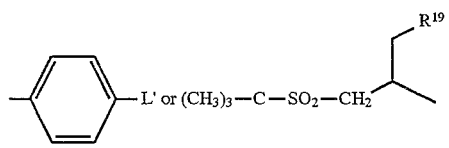

in which

L' independently has any of the abovementioned meanings of L, $R^{19}$ denotes phenyl or naphthyl, c denotes a number 0, 1, 2 or 3, d denotes a number 0, 1 or 2, $R^{10}$ has the abovementioned meaning of $R^9$ and is identical to or different from the latter, $R^{11}$ denotes methyl, or phenyl which is optionally substituted identically or differently up to 4 times by methyl or methoxy, or denotes a radical of the formula

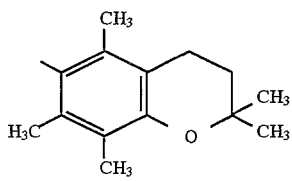

$R^2$, $R^3$ and $R^5$ are identical or different and denote Boc, hydrogen, methyl, ethyl, benzyloxycarbonyl or tert-butyl, $R^4$ represents hydrogen, nitro, benzyloxycarbonyl, tert-butoxycarbonyl, or represents a radical of the formula —$SO_2R^{20}$, in which $R^{20}$ has the abovementioned meaning of $R^{11}$ and is identical to or different from the latter, A represents a bond or a radical of the formula

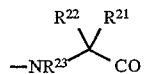

in which $R^{21}$ and $R^{22}$ are identical or different and have the abovementioned meaning of $R^{13}$ and $R^{14}$ and are identical to or different from the latter, $R^{23}$ has the abovementioned meaning of $R^2$, $R^3$ or $R^5$ and is identical to or different from the latter, $R^6$ represents formyl or carboxyl, or represents straight-chain or branched alkoxycarbonyl having up to 4 carbon atoms, or represents a radical of the formula —$CH_2$—$OR^{24}$ or —$CH(OR^{25})_2$, in which $R^{24}$ and $R^{25}$ are identical or different and denote hydrogen, straight-chain or branched alkyl having up to 3 carbon atoms, or benzyl.

4. A compound according to claim 1, of the formula

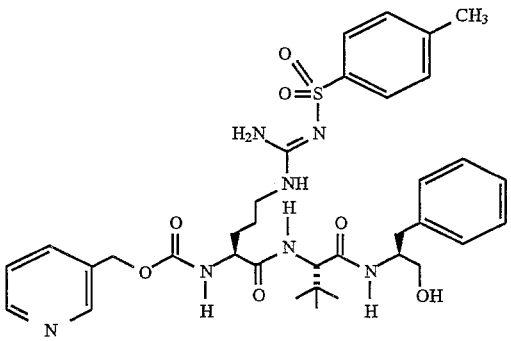

or a pharmaceutically acceptable salt thereof.

5. An artificial composition comprising an antivirally effective amount of a compound or salt thereof according to claim 1 and a diluent.

6. A method of combatting viruses which comprises administering to such viruses or to a virus host an antivirally effective amount of a compound or salt thereof according to claim 1.

7. A method of combatting viruses in a patient in need thereof which comprises administering to such patient an antivirally effective amount of a compound or salt thereof according to claim 4.

8. The compound according to claim 1 wherein $R^1$ is selected from the group consisting of benzyloxycarbonyl, 3,4-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, allyloxycarbonyl, vinyloxycarbonyl, 2-nitrobenzyloxycarbonyl, 3,4,5-trimethoxybenzyloxycarbonyl, cyclohexyloxycarbonyl, 1,1-dimethyloxycarbonyl adamantylcarbonyl, phthaloyl, 2,2,2-trichloroethoxycarbonyl, 2,2,2-trichloro-tert-butoxycarbonyl, menthyloxycarbonyl, phenoxycarbonyl, 4-nitrophenoxycarbonyl, fluoroenyl-9-methoxycarbonyl, formyl, acetyl, propionyl, pivaloyl, 2-chloroacetyl, 2-bromoacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl or 4-nitrophenyl.

9. The compound according to claim 1 wherein $R^1$ is tert-butoxycarbonyl (Boc) or benzyloxycarbonyl (Z).

* * * * *

UNITED STATES PATENT AND TRADEMARK OFFICE
CERTIFICATE OF CORRECTION

PATENT NO. : 5,646,121
DATED : July 8, 1997
INVENTOR(S) : Habich, et al.

It is certified that error appears in the above-indentified patent and that said Letters Patent is hereby corrected as shown below:

Title Page      FOREIGN PATENT DOCUMENTS: Delete "217103 " and substitute -- 2171103 --

Col. 67, line 30      Delete " he " and substitute -- be --

Signed and Sealed this

Twelfth Day of May, 1998

*Attest:*

BRUCE LEHMAN

*Attesting Officer*      *Commissioner of Patents and Trademarks*